US009649062B2

(12) United States Patent
Oku et al.

(10) Patent No.: US 9,649,062 B2
(45) Date of Patent: May 16, 2017

(54) SWALLOWING ESTIMATION DEVICE, INFORMATION TERMINAL DEVICE, AND STORAGE MEDIUM

(71) Applicants: HYOGO COLLEGE OF MEDICINE, Nishinomiya-shi (JP); EuSense Medical Co., Ltd., Nishinomiya-shi (JP)

(72) Inventors: Yoshitaka Oku, Nishinomiya (JP); Yoshihiko Oke, Nishinomiya (JP)

(73) Assignees: HYOGO COLLEGE OF MEDICINE, Nishinomiya-Shi (JP); EUSENSE MEDICAL CO., LTD., Nishinomiya-Shi (JP)

(*) Notice: Subject to any disclaimer, the term of this patent is extended or adjusted under 35 U.S.C. 154(b) by 0 days.

(21) Appl. No.: 15/011,672

(22) Filed: Feb. 1, 2016

(65) Prior Publication Data
US 2016/0143575 A1 May 26, 2016

Related U.S. Application Data

(63) Continuation of application No. PCT/JP2014/062239, filed on May 7, 2014.

(30) Foreign Application Priority Data

Aug. 26, 2013 (JP) ................. 2013-174949

(51) Int. Cl.
*A61B 5/00* (2006.01)
*A61B 5/08* (2006.01)
(Continued)

(52) U.S. Cl.
CPC .............. *A61B 5/4205* (2013.01); *A61B 5/08* (2013.01); *A61B 5/087* (2013.01); *A61B 5/1114* (2013.01);
(Continued)

(58) Field of Classification Search
CPC ......... A61B 5/4205; A61B 5/08; A61B 7/003; A61B 7/008
See application file for complete search history.

(56) References Cited

U.S. PATENT DOCUMENTS 7,749,177 B2 * 7/2010 Chau ..................... A61B 5/11
600/593
8,118,758 B2 * 2/2012 Kandori .................. A61B 5/11
600/593
(Continued)

FOREIGN PATENT DOCUMENTS

JP 2003-111748 4/2003
JP 2003111748 A * 4/2003
(Continued)

OTHER PUBLICATIONS

International Search Report for corresponding International Application No. PCT/JP2014/062239, Aug. 5, 2014.
(Continued)

*Primary Examiner* — Meredith Weare
(74) *Attorney, Agent, or Firm* — Mori & Ward, LLP

(57) ABSTRACT

A swallowing estimation device includes: a sound detection part configured to detect sound of a larynx portion; a respiration detection part configured to detect respiration; and a swallowing estimation part configured to estimate swallowing based on sound information outputted from the sound detection part and based on respiration information outputted from the respiration detection part. The swallowing estimation part obtains a value of a parameter for swallowing estimation with respect to a biological sound generation interval that corresponds to a respiratory cessation interval longer than or equal to 400 msec, and estimates whether swallowing has occurred in the biological sound generation interval based on whether the obtained value of
(Continued)

the parameter satisfies a swallowing determination condition.

9 Claims, 15 Drawing Sheets

(51) Int. Cl.
*A61B 7/00* (2006.01)
*A61B 5/087* (2006.01)
*A61B 5/11* (2006.01)

(52) U.S. Cl.
CPC ............... *A61B 7/00* (2013.01); *A61B 7/003* (2013.01); *A61B 7/008* (2013.01)

(56) References Cited

U.S. PATENT DOCUMENTS

| | | | |
|---|---|---|---|
| 9,138,171 B2* | 9/2015 | Chau | A61B 5/11 |
| 2005/0283096 A1* | 12/2005 | Chau | A61B 5/11 600/593 |
| 2008/0269646 A1* | 10/2008 | Chau | A61B 5/11 600/595 |
| 2009/0227907 A1* | 9/2009 | Kandori | A61B 5/11 600/593 |
| 2011/0160615 A1* | 6/2011 | Matsumura | A61B 5/4205 600/587 |
| 2011/0213620 A1* | 9/2011 | Dziubinski | G06F 19/322 705/2 |
| 2013/0253357 A1* | 9/2013 | Moussavi | A61B 5/4818 600/529 |
| 2013/0310661 A1* | 11/2013 | Jedwab | A61B 5/1107 600/301 |

FOREIGN PATENT DOCUMENTS

| | | | |
|---|---|---|---|
| JP | 2009-213592 | | 9/2009 |
| JP | 2011-4968 | | 1/2011 |
| JP | 2011004968 A | * | 1/2011 |
| JP | 2013-17694 | | 1/2013 |

OTHER PUBLICATIONS

Tsujimura et al., "Non-restrictive monitoring of swallowing frequency of elderly individuals", The Journal of Japanese Occupational Therapy Association, Feb. 15, 2012, vol. 31, No. I, pp. 52 to 59.

The International Preliminary Report on Patentability (Chapter I) with translation of Written Opinion of the International Searching Authority for corresponding International Application No. PCT/JP2014/062239, Aug. 5, 2014.

Oku, "Enge Igaku Basic Science Enge to Kokyu no Shinkei Chosetsu Kiko", "Deglutition", The official Journal of The Society of Swallowing and Dysphagia of Japan, Mar. 15, 2013, pp. 47 to 52, vol. 2, No. 1.

* cited by examiner

FIG. 9A  BIOLOGICAL SOUND DATA
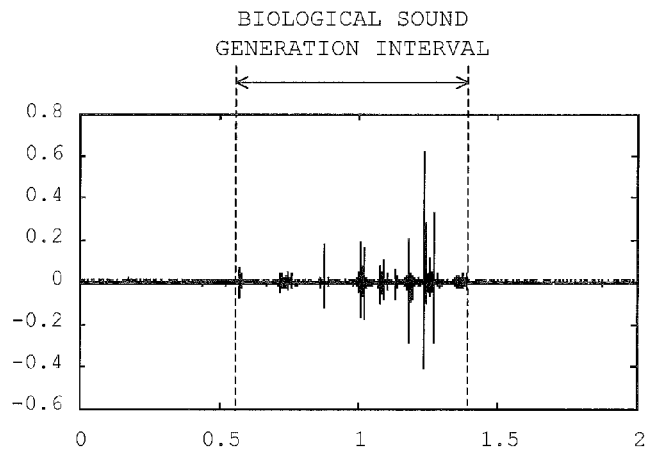
FIG. 9B  AIRFLOW PRESSURE DATA
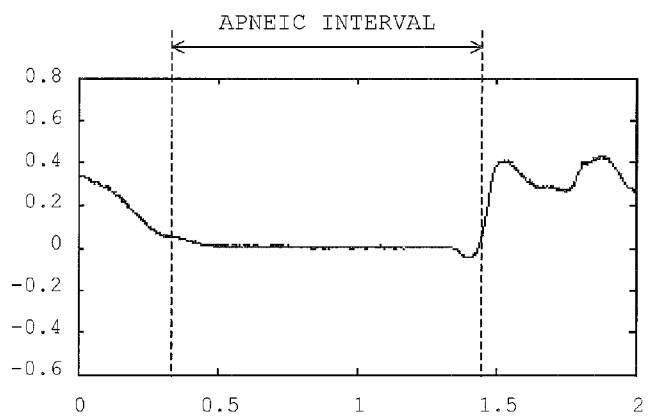
FIG. 9C  HYOID BONE DISPLACEMENT DATA
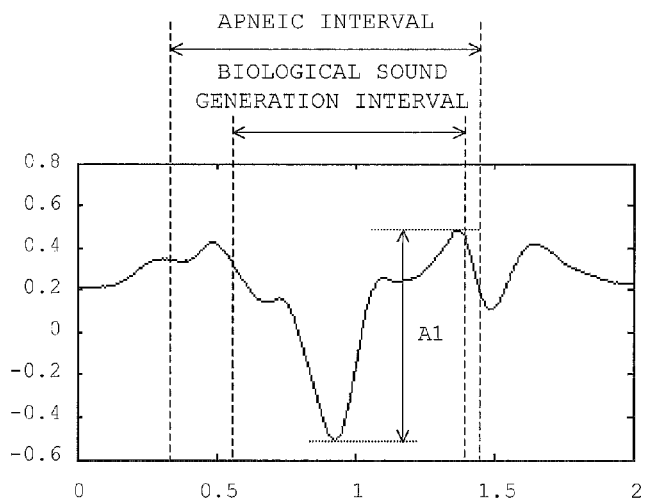

FIG. 13A

| THE NUMBER OF SWALLOWS | ... |
| THE NUMBER OF INSPIRATIONS-SWALLOWS | ... |
| THE NUMBER OF SWALLOWS-INSPIRATIONS | ... |
| THE NUMBER OF ASPIRATION RISKS | ... |

MODIFICATION 1

S205 → EXTRACT BIOLOGICAL SOUND GENERATION INTERVAL BASED ON COMPONENT OF BIOLOGICAL SOUND 750 Hz OR HIGHER, NUMBER OF PULSES, AND MAXIMUM PULSE WIDTH (S301) → S207

FIG. 13C

| | 3 ELEMENTS (EMBODIMENT 2) | WITHOUT SOUND (COMPARATIVE EXAMPLE 1) | WITHOUT RESPIRATION (COMPARATIVE EXAMPLE 2) | WITHOUT HYOID BONE (MODIFICATION 1) |
|---|---|---|---|---|
| THE NUMBER OF EXTRACTED SWALLOWS | 27 | 27 | 27 | 27 |
| NON-EXTRACTIONS | 0 | 0 | 0 | 0 |
| ERRONEOUS EXTRACTIONS | 7 | 19 | 36 | 18 |
| TOTAL | 34 | 46 | 63 | 45 |

SWALLOWING ESTIMATION DEVICE, INFORMATION TERMINAL DEVICE, AND STORAGE MEDIUM

CROSS REFERENCE TO RELATED APPLICATION

This application is a continuation of International Application No. PCT/JP2014/62239 filed May 7, 2014, which claims priority to Japanese Patent Application No. 2013-174949 filed Aug. 26, 2013. The contents of these applications are incorporated herein by reference in their entirety.

BACKGROUND OF THE INVENTION

1. Field of the Invention

The present invention relates to a swallowing estimation device which estimates a swallowing movement, an information terminal device for obtaining information necessary for estimation of the swallowing movement, and a storage medium having stored therein a program which provides a computer with a swallowing estimation function.

2. Disclosure of Related Art

Japanese Laid-Open Patent Publication No. 2013-17694 discloses a technology which analyzes the frequency of biological sound obtained from a larynx portion, and distinguishes among swallowing, coughs and utterance based on frequency characteristics thereof. Meanwhile, "Non-restrictive monitoring of swallowing frequency of elderly individuals" in an academic journal "The Journal of Japanese Occupational Therapy Association" Vol. 31(1) PP. 52 to 59 (Non-patent literature) issued by the Japanese Association of Occupational Therapists in February in 2012 discloses the following technology. That is, with respect to pulse groups each consisting of pulses obtained by converting biological sound collected by a larynx microphone into pulses, a pulse group in which each pulse width is less than or equal to 60 msec and the number of pulses is less than or equal to 20 is determined as representing a swallowing movement.

Before performing swallowing estimation, first, it is necessary to collect information such as biological sound from a subject. In this case, in order not to restrict the subject as much as possible, it is desirable that the apparatus and the like to be worn by the subject are as simple as possible. Accordingly, it becomes possible to collect information for swallowing estimation from the subject in a living environment. However, when information is collected in a living environment in this manner, information of various sounds that contaminate swallowing sound is collected, such as household noises, sounds during eating and drinking, conversations, sounds generated when the neck is rotated, in addition to biological sound generated during swallowing. These noises cause erroneous swallowing estimation, resulting in reduced estimation accuracy of swallowing.

SUMMARY OF THE INVENTION

During swallowing, there is always a respiratory cessation (apnea) state for a predetermined period or longer. When this is focused on, it is desirable that a swallowing interval is estimated by performing analysis of a signal from an organism only with respect to an apneic interval that is longer than or equal to a predetermined period.

A first aspect of the present invention relates to a swallowing estimation device. The swallowing estimation device according to this aspect includes: a sound detection part configured to detect sound of a larynx portion; a respiration detection part configured to detect respiration; and a swallowing estimation part configured to estimate swallowing based on sound information outputted from the sound detection part and based on respiration information outputted from the respiration detection part. Here, the swallowing estimation part obtains a value of a parameter for swallowing estimation with respect to a biological sound generation interval that corresponds to an apneic interval longer than or equal to 400 msec, and estimates whether swallowing has occurred in the biological sound generation interval based on whether the obtained value of the parameter satisfies a swallowing determination condition.

A second aspect of the present invention relates to a swallowing estimation device. The swallowing estimation device according to this aspect includes: a biological sound detection means configured to detect biological sound at a larynx portion; respiration detection means configured to detect change in airflow of respiration; a signal intensity conversion means configured to convert biological sound data obtained by sampling the biological sound into signal intensity data; signal interval identification means configured to identify a signal interval having an intensity level higher than or equal to a noise level based on the signal intensity data; respiration identification means configured to identify an apneic interval based on airflow pressure data obtained by sampling change in the respiration; signal pulsing means configured to obtain a signal intensity that corresponds to a sampling timing in the apneic interval that is longer than or equal to a predetermined period and that overlaps the signal interval, and configured to generate a signal pulse having a width that corresponds to a period in which the signal intensity is greater than or equal to a predetermined level; swallowing reflex estimation means configured to estimate, as an estimated swallowing reflex interval, the apneic interval that satisfies a determination condition that the number of the signal pulses in the apneic interval longer than or equal to the predetermined period is less than or equal to a predetermined number and a width of each signal pulse in the apneic interval longer than or equal to the predetermined period is less than or equal to a predetermined period; and display means configured to display the estimated swallowing reflex interval.

A third aspect of the present invention relates to an information terminal device. The information terminal device according to this aspect includes: a sound detection part configured to detect sound of a larynx portion; a respiration detection part configured to detect respiration; and a storage part in which sound information outputted from the sound detection part and respiration information outputted from the respiration detection part are stored.

A fourth aspect of the present invention is a storage medium having stored therein a program which provides a computer with: a function of obtaining a value of a parameter for swallowing estimation, with respect to a biological sound generation interval that corresponds to an apneic interval longer than or equal to a predetermined period; and a function of estimating whether swallowing has occurred in the biological sound generation interval based on whether the obtained value of the parameter satisfies a swallowing determination condition.

BRIEF DESCRIPTION OF THE DRAWINGS

The above and other objects and new features of the present invention will be fully clarified by the following description of the embodiment, when read in conjunction with accompanying drawings.

FIG. 9A shows a biological sound data according to Embodiment 2;

FIG. 9B shows an airflow pressure data according to Embodiment 2;

FIG. 9C shows a hyoid bone displacement data according to Embodiment 2;

FIG. 13A shows a screen to be displayed on the display part according to Embodiment 2;

FIG. 13B is a flow chart showing operation performed by the information processing device according to Modification 1;

FIG. 13C shows estimation results obtained when swallowing estimation was performed by actually collecting information for swallowing estimation;

It should be noted that the drawings are solely for description and do not limit the scope of the present invention by any degree.

DESCRIPTION OF THE PREFERRED EMBODIMENTS

The present embodiment is characterized in that: an estimated swallowing reflex interval is constrained based on energy distribution of biological sound obtained from a larynx portion and based on information of change in airflow pressure caused by respiration; and the estimated swallowing reflex interval is further constrained to be specified based on information of displacement of the hyoid bone.

Embodiment 1

Figure 1:
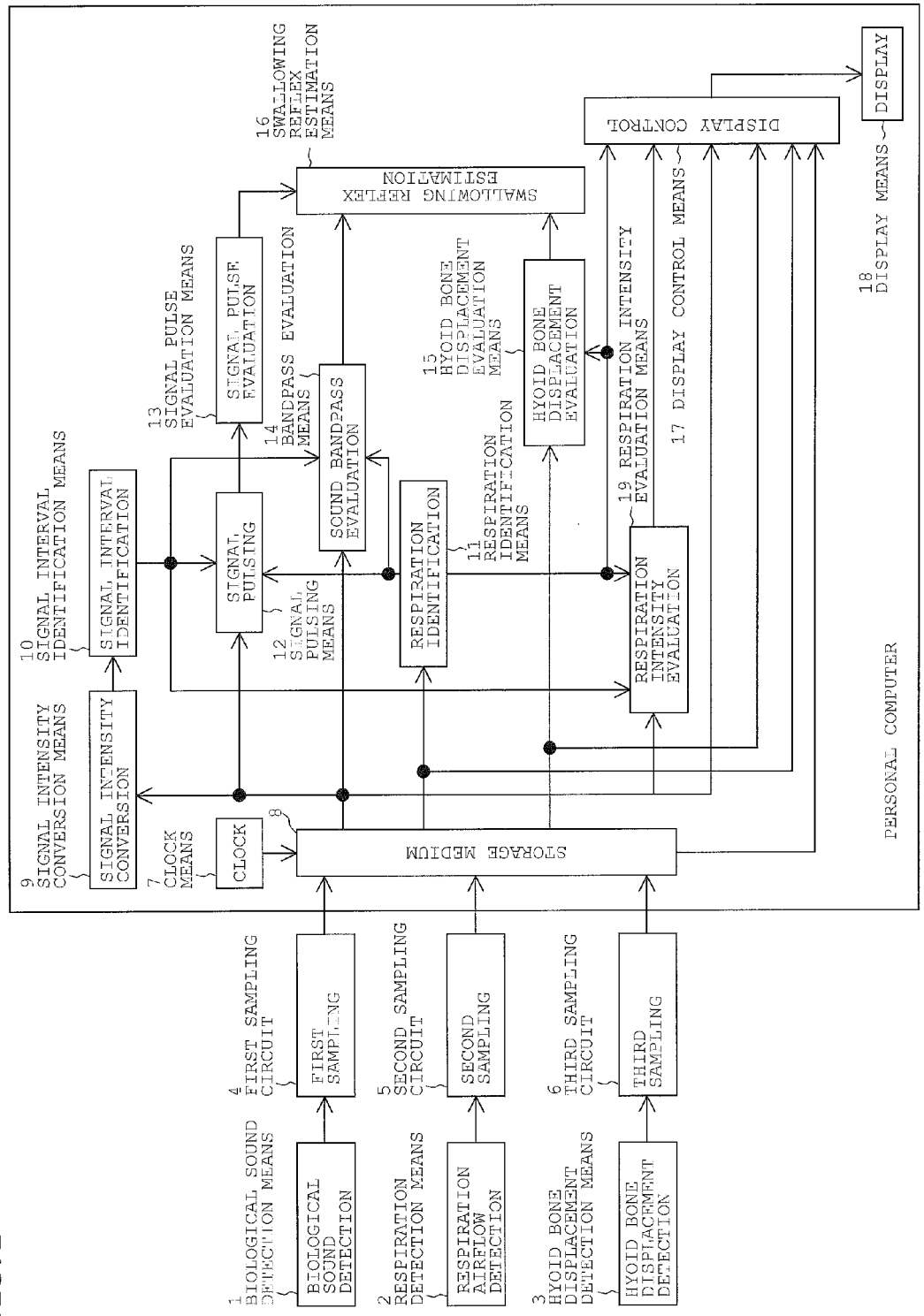
FIG. 1 is a functional block diagram showing a configuration and a function of a swallowing activity monitoring device according to Embodiment 1.

FIG. 1 shows a circuit block diagram for explaining operation performed in Embodiment. However, the blocks in a personal computer are not actual circuit blocks but functional blocks.

Hereinafter, operation performed during a data measurement period of the present embodiment will be described.

In the present embodiment, a microphone disposed close to the larynx portion functions as biological sound detection means 1 which detects sound in an organism, an air pressure sensor provided in a tube of a nasal cannula functions as respiration detection means 2 which detects change in airflow caused by respiration, and a piezoelectric sheet attached to the larynx portion functions as hyoid bone displacement detection means 3 which catches deformation of the larynx portion to detect displacement of the hyoid bone.

A biological sound signal obtained from the biological sound detection means 1, an airflow pressure signal obtained from the respiration detection means 2, and a hyoid bone displacement signal obtained from the hyoid bone displacement detection means 3 are inputted to their corresponding first sampling circuit 4, second sampling circuit 5, and third sampling circuit 6, respectively. Then, each signal is sampled at a cycle of 0.1 msec (10 kHz), and then subjected to A/D conversion. Then, biological sound data, airflow pressure data, and hyoid bone displacement data which have been obtained through the A/D conversion are stored in a storage medium 8 along with time data obtained from clock means 7. Accordingly, during a data measurement period, the biological sound data, the airflow pressure data, and the hyoid bone displacement data are stored in the storage medium 8, each paired with time data.

After the measurement period described above has ended, data processing as described below is performed in the personal computer.

First, signal intensity conversion means 9 converts, into signal intensity data, biological sound data which corresponds to a signal waveform read from the storage medium 8. Specifically, with the window function (sampling range) set to 1.5 seconds, biological sound data is cut out to be subjected to short-time Fourier transform processing, and then, the total sum of the amplitudes is obtained, whereby the biological sound data is converted into signal intensity data. At this time, an appropriate bandpass filter process may be performed.

Since this short-time Fourier transform processing is performed with the sampling range shifted by 0.2 seconds, signal intensity data having a temporal resolution of 1/2000 of that of the biological sound data is outputted. This signal intensity data is used to exclude soundless intervals. By setting the window function to be wide and also setting the shift interval to be large, load on the calculation processing is reduced.

Signal interval identification means 10 compares the signal intensity data with a first reference value L1, to generate an identification output for identifying a signal interval having an intensity level higher than or equal to a noise level. That is, the signal interval identification means considers that swallowing has not occurred in a low-level interval where only noise is present and that swallowing has occurred in a high-level interval, thereby specifying the high-level interval as a signal interval.

Respiration identification means 11 issues respiration identification outputs which respectively represent three types of intervals of airflow pressure data, i.e., expiration interval, respiratory pause (late expiration) interval, and inspiration interval.

Signal pulsing means 12 extracts biological sound data that corresponds to an apneic interval greater than or equal to a second reference value L2 (for example, 0.6 seconds) in the signal interval, and performs continuous wavelet transform processing on the extracted biological sound data to obtain the total sum of frequency spectrum intensities. Then, the signal pulsing means 12 compares the obtained total sum with a third reference value L3, and then, outputs a signal pulse having a width that corresponds to a period having an intensity value greater than or equal to the reference value.

When the width of each of all the signal pulses in the apneic interval greater than or equal to the second reference value L2 in the signal interval is less than or equal to a fourth reference value L4 (for example, 25 msec) and the number of the signal pulses is less than or equal to a fifth reference value L5 (for example, 20), signal pulse evaluation means 13 estimates that there is a high possibility that the signal interval is a swallowing reflex interval, and issues a first estimation output. In the non-patent literature mentioned above, the signal pulse width during swallowing is set to be less than or equal to 60 msec. However, in the present embodiment, since the third reference value L3 is set to a large value, the signal pulse width is small, and the fourth reference value L4 is set to 25 msec.

Next, bandpass evaluation means 14 converts the biological sound data into a mel-frequency spectrogram in the apneic interval greater than or equal to the second reference value L2 in the signal interval. Then, with respect to the mel-frequency spectrogram, when the proportion of the total sum of spectrum levels of high range components (for example, higher than or equal to 750 Hz) in the apneic interval to the total sum of spectrum levels in the apneic interval is greater than or equal to a sixth reference value L6 (for example, 15%), the bandpass evaluation means 14 estimates that there is a high possibility that the signal interval is a swallowing reflex interval, and issues a second estimation output.

Further, hyoid bone displacement evaluation means 15 specifies the maximum value of the hyoid bone displacement data in the measurement period. Then, when hyoid bone displacement data whose proportion to the maximum value is greater than or equal to a seventh reference value L7 (for example, 10%) is present in the apneic interval greater than or equal to the second reference value L2 in the signal interval, the hyoid bone displacement evaluation means 15 estimates that there is a high possibility that the signal interval is a swallowing reflex interval, and issues a third estimation output.

In the present embodiment, swallowing reflex estimation means 16 generates an output that specifies the signal interval as an estimated swallowing reflex interval, only when all of the first estimation output, the second estimation output, and the third estimation output have been generated.

The estimated swallowing reflex interval specified as above is displayed via display control means 17 as shown in FIGS. 2A to 2D on display means 18 which is a monitor screen of the personal computer. On the display means 18, in accordance with a time scale indicated in a reduced manner, a biological sound signal waveform in FIG. 2A, an airflow pressure signal waveform in FIG. 2B, a hyoid bone displacement signal waveform in FIG. 2C, and a biological sound signal intensity waveform in FIG. 2D of the entire measurement period are displayed as a basic screen along with the time scale.

Figure 2:
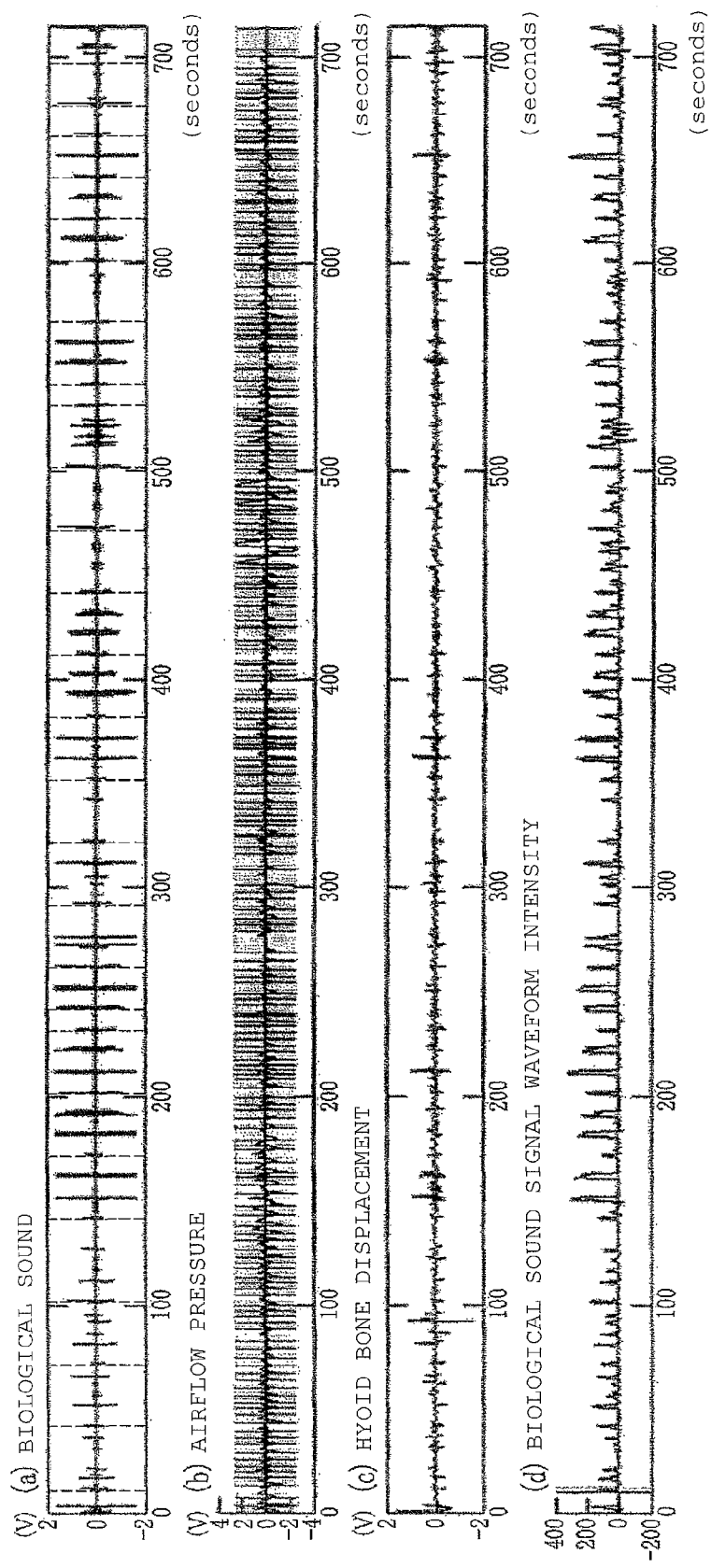
FIG. 2 shows a display example of each waveform in an estimated swallowing reflex interval obtained by the swallowing activity monitoring device according to Embodiment 1.

In FIG. 2A, each vertical broken line indicates an estimated swallowing reflex position. With respect to the airflow pressure waveform shown in FIG. 2B, in an actual display, the respiration identification outputs which respectively represent three types of intervals of airflow pressure data, i.e., expiration interval, respiratory pause interval, and inspiration interval, are colored differently and indicated with vertical lines, so that the respective types of outputs can be recognized by viewing.

In this state, when an operator points at an estimated swallowing reflex position in the basic screen, the biological sound signal waveform, the airflow pressure signal waveform, and the hyoid bone displacement signal waveform of an apneic interval corresponding to the pointed position and several respiration periods before and after the apneic interval are displayed as a sub-screen, along with the time scale.

The estimated swallowing reflex interval above is displayed in various manners in order to indicate a swallowing state of aspiration or a high aspiration risk.

For example, after normal swallowing, the expiratory sound intensity is less than or equal to a half of the inspiratory sound intensity, but after abnormal swallowing, the expiratory sound intensity is increased. With this focused on, a sub-screen is displayed as explained below.

Respiratory sound intensity evaluation means 19 performs short-time Fourier transform individually on biological sound data for each of eight intervals in total, i.e., four cycles of the expiration intervals and the inspiration intervals before and after the estimated swallowing reflex interval, and obtains the total sum for each interval as signal intensity data. Further, when the average signal intensity of the expiration intervals/the average signal intensity of the inspiration intervals after the estimated swallowing reflex interval has increased to exceed 50% of that before the estimated swallowing reflex interval, the respiratory sound intensity evaluation means 19 determines the interval as an estimated aspiration interval, and inputs alert information to the display control means 17. When the operator selects the estimated aspiration interval, the display control means 17 causes the display means 18 to display a sub-screen for the estimated aspiration interval instead of the sub-screen for the estimated swallowing reflex interval described above.

When diagnosing swallowing, the respiration states before and after an estimated swallowing reflex interval can be used as a reference. With this focused on, the display control means 17 determines whether each of the respirations before and after an estimated swallowing reflex interval is an expiration interval or an inspiration interval, expresses the result in four types, and additionally displays the frequency thereof in the basic screen on the display means 18, as shown in FIG. 3, for example.

Figure 3:
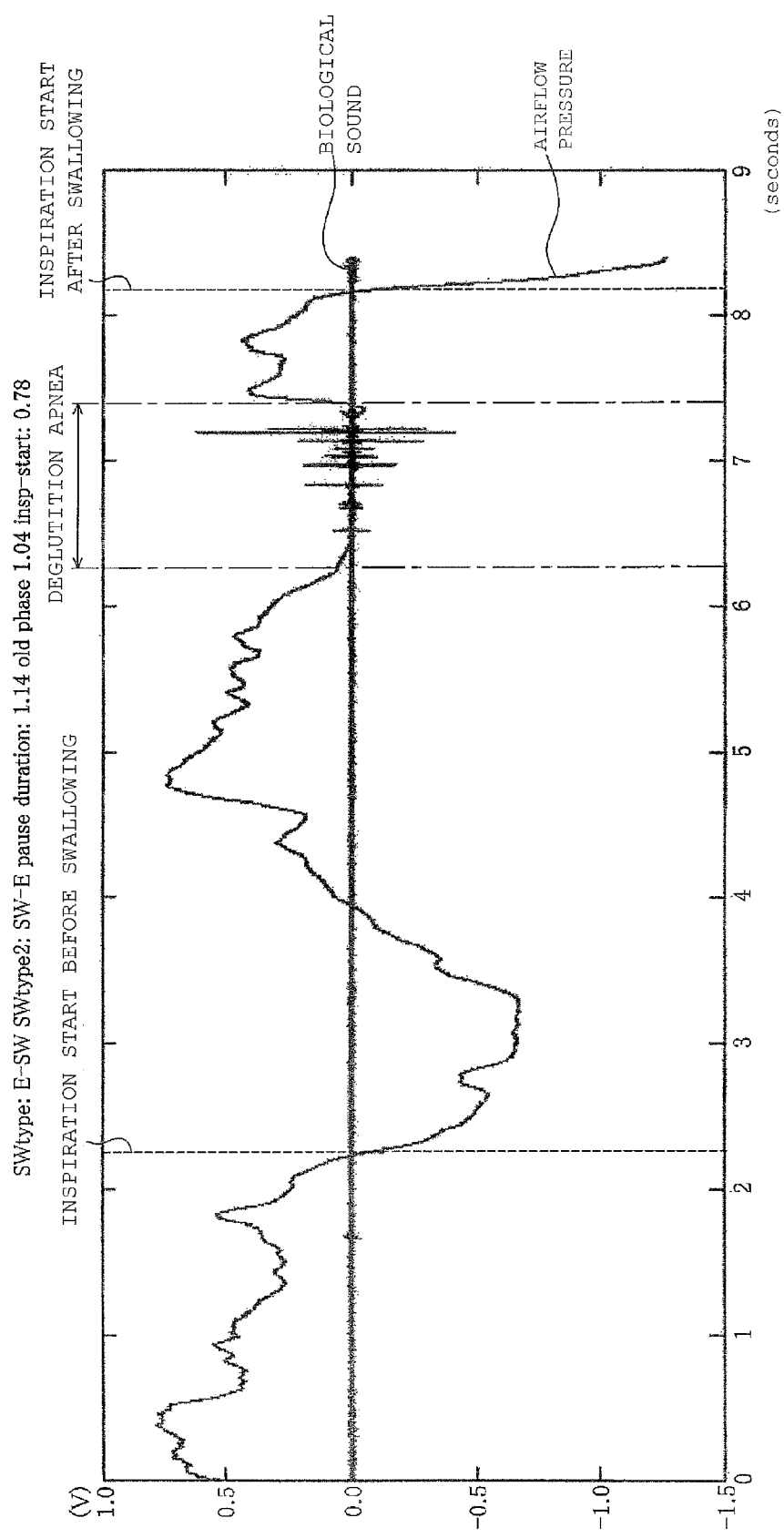
FIG. 3 shows a display example of a biological sound waveform and an airflow sound waveform shown on a fine time scale in a superposed and zoomed-in manner in the swallowing activity monitoring device according to Embodiment 1.

The display example shown in FIG. 3 indicates the following: swallowing occurred in expiration (SWtype: E-SW); respiration after the swallowing started with expiration (SWtype2: SW-E); when the average respiration interval is assumed as 1, the swallowing start point is the time point when 1.04 has elapsed from the inspiration start (old phase: 1.04); and latency before inspiration starts after the swallowing is 0.78 seconds (insp-start: 0.78). The broken vertical lines in FIG. 3 each represents a start position of inspiration, and the (interval between) dash-dot vertical lines represents a deglutition apnea period.

The indication of the estimated swallowing reflex interval in the present embodiment is not limited to the manner described above, and includes various types of indication modes relevant to the estimated swallowing reflex interval. In particular, indication of aspiration risk estimation is important among indications of swallowing reflex estimation.

In the present embodiment, the swallowing reflex estimation means 16 estimates the estimated swallowing reflex interval, based on all of the first estimation output, the second estimation output, and the third estimation output. However, the estimation in the present embodiment may be made only based on the first estimation output, or may be made based on the first estimation output and the second estimation output.

In addition, the reference values used in the present embodiment are for adjusting the degree of constraining the estimated swallowing reflex interval, are not intended to limit the values and ranges in the present embodiment, and should be adjusted as appropriate.

Embodiment 2

Embodiment 2 is a more specific example of the configuration and the processes according to Embodiment 1.

In Embodiment 2, a swallowing estimation system 100 corresponds to the "swallowing estimation device" set forth in claims. A sound sensor 231a corresponds to the "sound detection part" set forth in claims. A pressure sensor 215 corresponds to the "respiration detection part" set forth in claims. A control part 313 corresponds to the "swallowing estimation part" set forth in claims. A displacement sensor 231b corresponds to the "displacement detection part" set forth in claims. A speaker 312, the control part 313, and a display part 320 correspond to the "output part" set forth in claims. A hard disk 314 corresponds to the "storage part" set forth in claims. An input part 330 corresponds to the "input part" set forth in claims. A terminal device 210 corresponds to the "information terminal device" set forth in claims. However, the correspondence between the present embodiment and the claims is merely one example and does not limit the invention according to the claims to the present embodiment.

Figure 4:
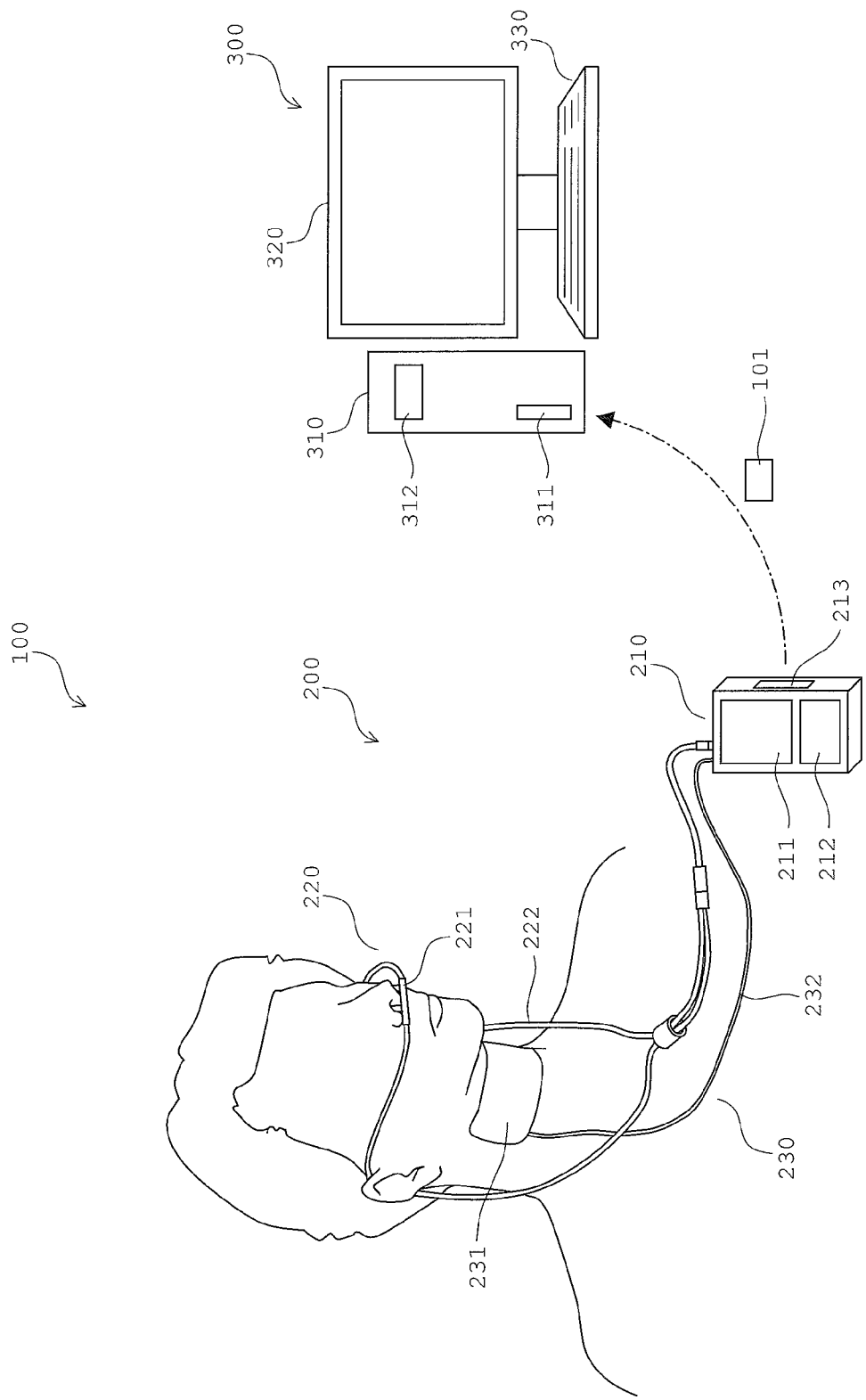
FIG. 4 is an external view showing a configuration of a swallowing estimation system according to Embodiment 2.

FIG. 4 is an external view showing a configuration of the swallowing estimation system 100 according to the present embodiment. The swallowing estimation system 100 includes a measurement device 200 and an information processing device 300. In the swallowing estimation system 100, a small storage medium 101 (for example, SD card) which is easy to be carried is used. The measurement device 200 includes the terminal device 210, a nasal cannula 220, and a detection part 230.

The terminal device 210 includes a display part 211 and an input part 212, and is configured to be small and light in weight so that a subject can always wear the terminal device 210. While confirming the display of the display part 211, the subject inputs an instruction to a control part 214 (see FIG. 5) through an input part 212 which includes buttons and adjustment knobs. The terminal device 210 includes a writing part 213 which performs writing on a storage medium 101.

The nasal cannula 220 includes an attachment part 221 having a pair of tube-like members, and tubes 222 connected to opposite ends of the attachment part 221. The pair of tube-like members of the attachment part 221 are inserted into the nasal cavities of a patient, and the other ends of the tubes 222 are connected to the terminal device 210. Accordingly, when a patient breathes, air in the tubes 222 flows, and the flow of the air in the tubes 222 is detected as a pressure by the pressure sensor 215 (see FIG. 5) in the terminal device 210. Even when the patient is breathing through the mouth, since the nasal cavities are connected to the oral cavity, the air in the tubes 222 flows and the pressure changes.

The detection part 230 includes a pad 231 which is thin and flexible, and a cable 232. The pad 231 is attached to the larynx portion of the subject. The pad 231 includes: the sound sensor 231a (see FIG. 5) for detecting sound of the larynx portion; and the displacement sensor 231b (FIG. 5) for detecting, based on the pressure, displacement of the hyoid bone depending on deformation of the larynx portion.

The information processing device 300 includes a body 310, the display part 320, and the input part 330. The body 310 includes a reading part 311 which performs reading from the storage medium 101, and the speaker 312 for outputting sound. The operator inputs an instruction to the control part 313 (see FIG. 5) by using the input part 330 which includes a keyboard and a mouse. The display part 320 is composed of a display, and displays a swallowing estimation result and the like described later.

Figure 5:
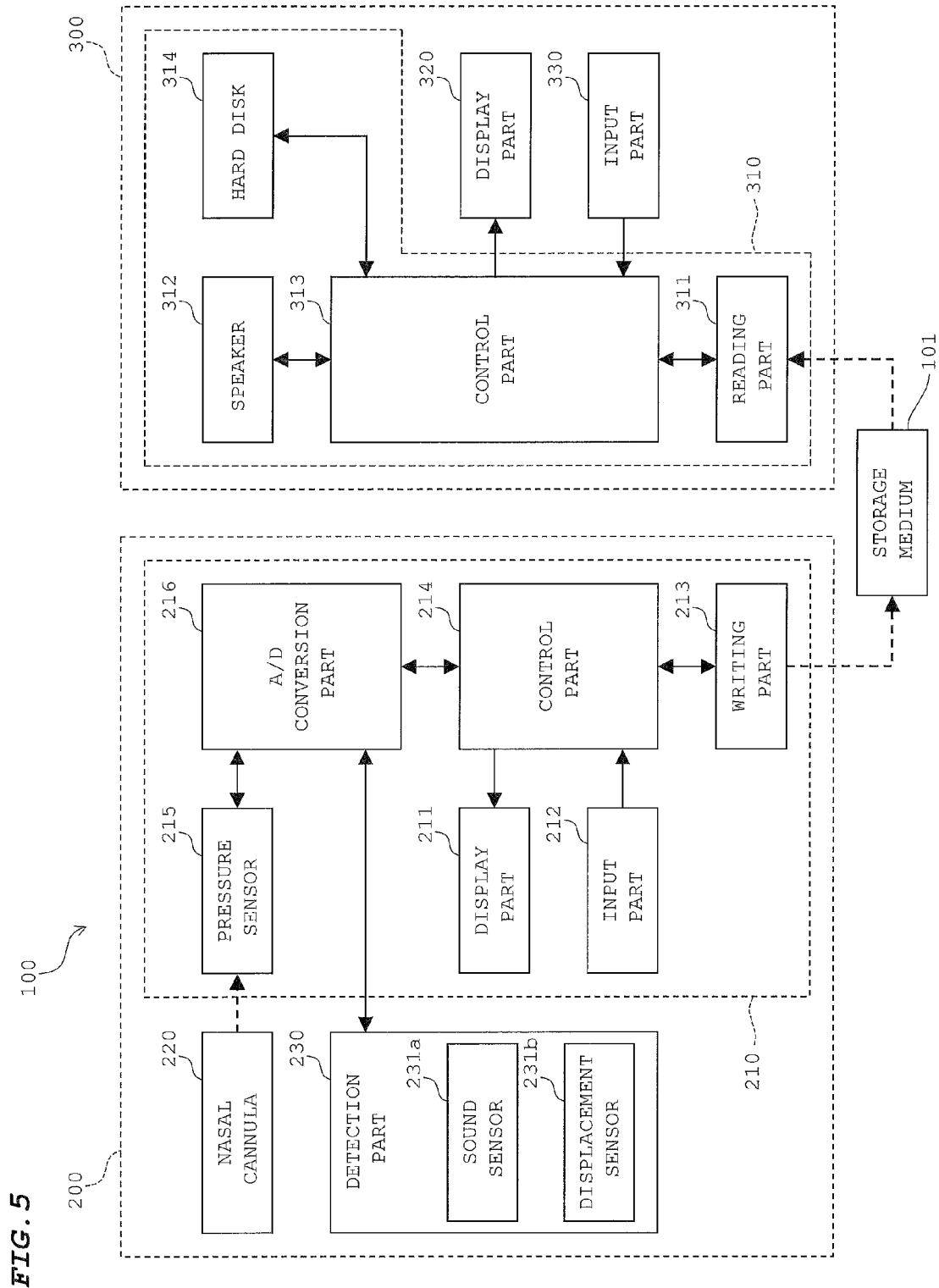
FIG. 5 is a block diagram showing a configuration of the swallowing estimation system according to Embodiment 2.

FIG. 5 is a block diagram showing a configuration of the swallowing estimation system 100.

The terminal device 210 includes the control part 214, the pressure sensor 215, and an A/D conversion part 216, in addition to the display part 211, the input part 212, and the writing part 213 which are shown in FIG. 4.

The pressure sensor 215 detects, as a pressure, the flow of the air guided via the tubes 222 of the nasal cannula 220, and outputs the detected analog pressure signal to the A/D conversion part 216. The detection part 230 includes the sound sensor 231a and the displacement sensor 231b. The sound sensor 231a detects sound in the vicinity of the larynx portion of the subject, and outputs the detected analog sound signal to the A/D conversion part 216. The displacement sensor 231b detects deformation of the larynx portion of the subject as displacement of the hyoid bone, and outputs the detected analog displacement signal to the A/D conversion part 216. The A/D conversion part 216 samples the pressure signal, the sound signal, and the displacement signal in predetermined cycles, and outputs digital signals corresponding to the respective sampled signals to the control part 214. The respective pieces of data obtained by performing A/D conversion on the sound signal, the pressure signal, and the displacement signal correspond to the "biological sound data", the "airflow pressure data", the "hyoid bone displacement data" in Embodiment 1, respectively.

The control part 214 controls the components of the terminal device 210. Moreover, the control part 214 writes, along with time data, each data outputted from the A/D conversion part 216 into the storage medium 101 set in the writing part 213. The time data is counted by a clock circuit built in the control part 214. When measurement by the measurement device 200 has ended, the storage medium 101 is taken out of the writing part 213, and is set in the reading part 311 of the information processing device 300.

The body 310 is composed of a personal computer, for example, and includes the control part 313 and the hard disk 314, in addition to the reading part 311 and the speaker 312 which are shown in FIG. 4. The control part 313 controls the components of the body 310, receives an instruction inputted via the input part 330, outputs an image signal to the display part 320 in response to the instruction, and outputs sound from the speaker 312. Moreover, the control part 313 reads data from the storage medium 101 set in the reading part 311, and stores the data in the hard disk 314. Further, the control part 313 performs calculation based on the data and a program stored in the hard disk 314. The program stored in the hard disk 314 provides the control part 313 with a swallowing estimation function described later. This program may be previously installed in the hard disk 314, or may be downloaded to the hard disk 314 from a disk medium or the Internet. In this case, the reading part 311 is provided with a disc drive to read this program from the disc.

Figure 6:
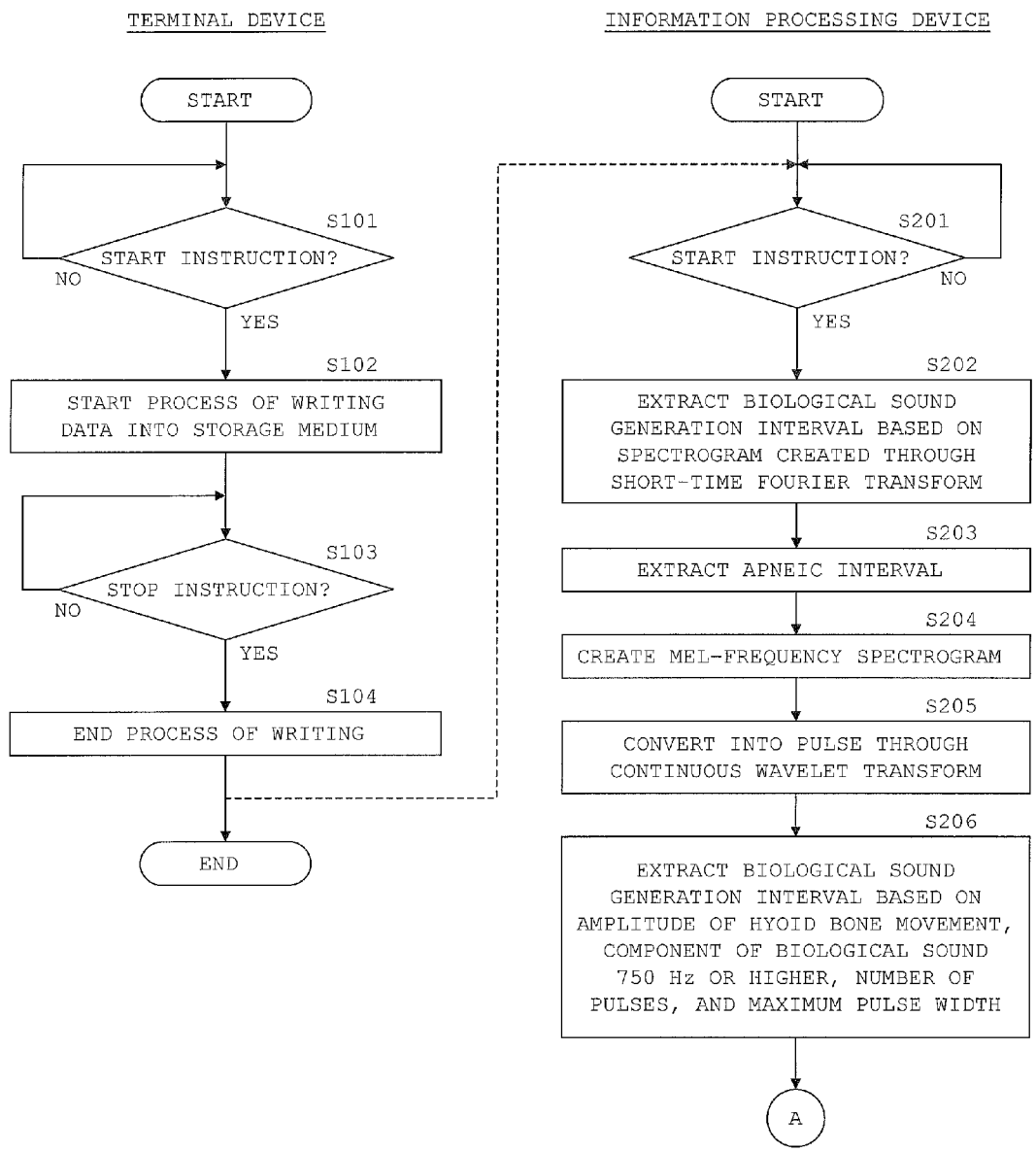
FIG. 6 is a flow chart showing operations performed by a terminal device and an information processing device according to Embodiment 2.
Figure 7:
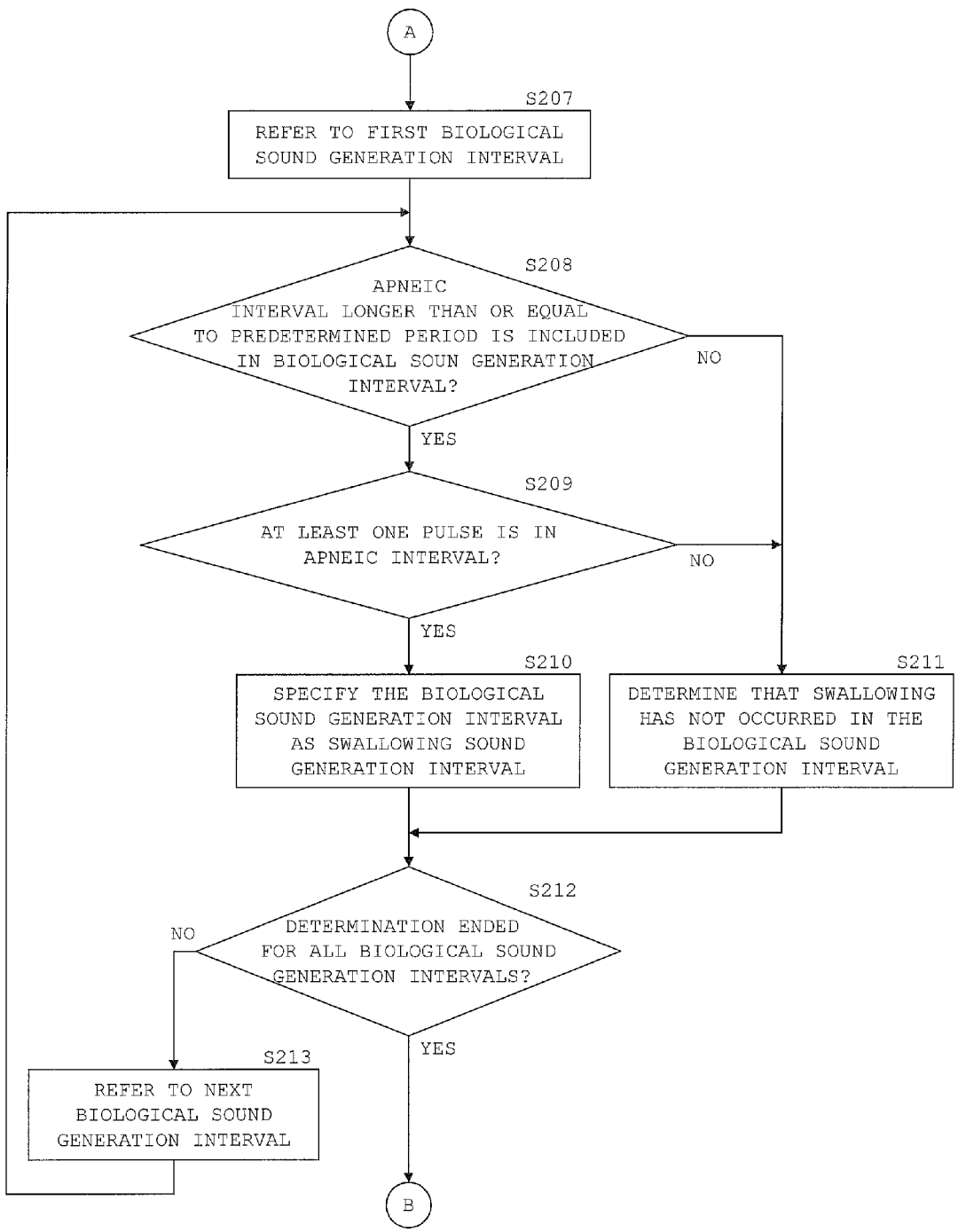
FIG. 7 is a flow chart showing operation performed by the information processing device according to Embodiment 2.
Figure 8:
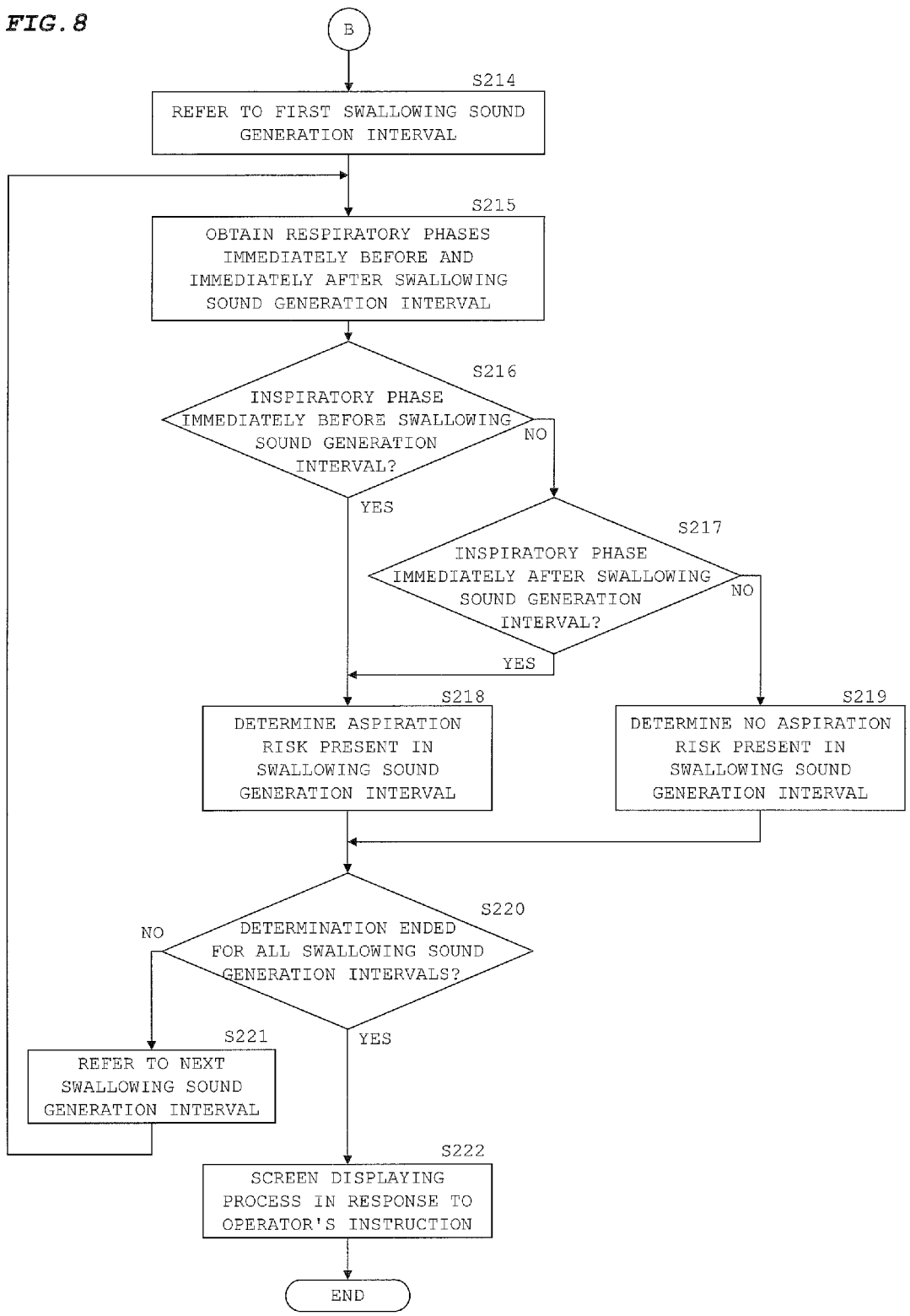
FIG. 8 is a flow chart showing operation performed by the information processing device according to Embodiment 2.

FIG. 6 to FIG. 8 are flow charts showing operations performed by the terminal device 210 and the information processing device 300.

With reference to FIG. 6, upon receiving a start instruction via the input part 212 (S101: YES), the control part 214 of the terminal device 210 obtains biological sound data, airflow pressure data, and hyoid bone displacement data, and starts a process of writing the obtained data in the storage medium 101 (S102). Then, upon receiving a stop instruction via the input part 212 (S103: YES), the control part 214 ends the writing process (S104). Accordingly, the process of the terminal device 210 ends. The storage medium 101 in which the data has been written is transferred to the information processing device 300 as described above.

FIGS. 9A to 9C respectively show the biological sound data, the airflow pressure data, and the hyoid bone displacement data written in the storage medium 101, for a predetermined period, as the waveforms of analog signals before being subjected to A/D conversion. In FIGS. 9A to 9C, signals in 2 seconds are extracted and shown. However, actually, data corresponding to a period for which the writing process has been performed is stored in the storage medium 101. "Biological sound generation interval" shown in FIGS. 9A and 9C and "apneic interval" shown in FIGS. 9B and 9C will be described later.

With reference back to FIG. 6, upon receiving a start instruction via the input part 330 (S201: YES) after having stored the biological sound data, the airflow pressure data, and the hyoid bone displacement data into the hard disk 314, the control part 313 of the information processing device 300 performs the process below.

Figure 10A:
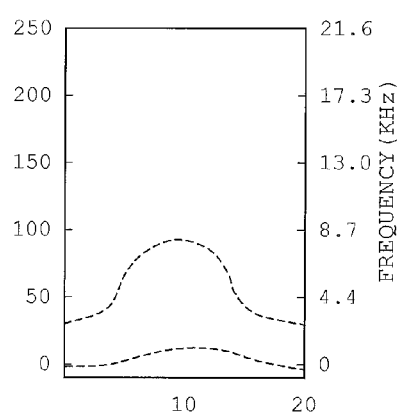
FIG. 10A schematically shows a spectrogram according to Embodiment 2.

The control part 313 creates a spectrogram by performing short-time Fourier transform on the biological sound data, and extracts biological sound generation intervals based on the created spectrogram (S202). Specifically, with respect to the biological sound data of the entire interval, the control part 313 sets the window function (sampling range) to 1.5 seconds to cut out biological sound data, and performs short-time Fourier transform on the cut-out biological sound data to create a spectrogram as shown in FIG. 10A. That is, Fourier transform is performed in a unit time (time width of 1.5 seconds), and this is sequentially performed with 0.2 seconds shifted every time, whereby a spectrogram is created. The example shown in FIG. 10A is a spectrogram created for 20 unit-time widths, that is, for 4 seconds. Then, the control part 313 obtains the total sum of the amplitudes of the created spectrogram to perform conversion into signal intensity data, and extracts, as a biological sound generation interval, each interval that has a value exceeding the noise average+2SD (standard deviation). Accordingly, with respect to the biological sound data of the entire interval, biological sound generation intervals are specified. FIGS. 9A and 9C additionally show a biological sound generation interval extracted in this manner.

Next, with respect to the airflow pressure data, the control part 313 extracts, as an apneic interval, each interval that has a value less than or equal to a threshold that is set in consideration of noise (S203). Accordingly, with respect to the airflow pressure data of the entire interval, apneic intervals are set. FIG. 9B additionally shows an apneic interval extracted in this manner.

Figure 10C:
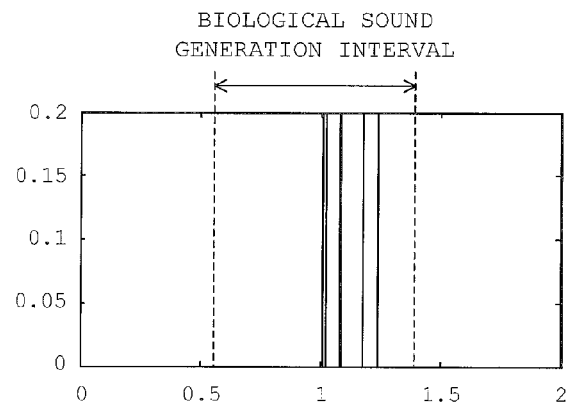
FIG. 10C shows pulses obtained through continuous wavelet transform according to Embodiment 2.
Figure 10B:
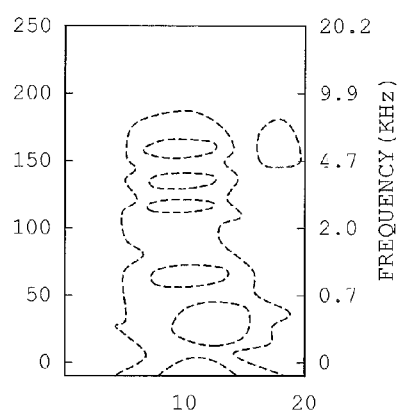
FIG. 10B schematically shows a mel-frequency spectrogram according to Embodiment 2.

Next, in each biological sound generation interval, the control part 313 creates a mel-frequency spectrogram as shown in FIG. 10B, from the spectrogram created in S202 (S204). In FIG. 10B, the vertical axis is expressed in the mel-scale. Thus, in the mel-frequency spectrogram shown in FIG. 10B, compared with the frequency spectrogram shown in FIG. 10A, the coordinate axis in low frequency bands is extended, and the coordinate axis in high frequency bands is compressed. Accordingly, the resolving power for 0.7-5.0 kHz bands is enhanced.

Figure 10D:
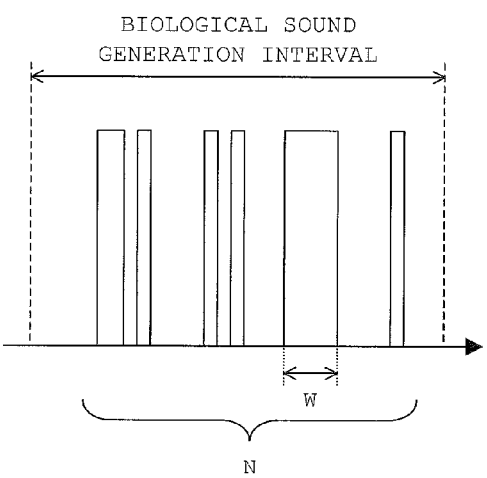
FIG. 10D schematically shows pulses obtained through continuous wavelet transform in a zoomed-in manner according to Embodiment 2.

Next, in each biological sound generation interval, the control part 313 performs continuous wavelet transform on the data obtained in S202 that has been subjected to the short-time Fourier transform, to convert the data into pulses (S205), thereby to generate the pulses as shown in FIG. 10C. In the example shown in FIG. 10C, the biological sound generation interval includes six pulses. In an enlarged schematic representation of these pulses, a plurality of pulses respectively having different widths are included as shown in FIG. 10D.

Next, from among the biological sound generation intervals extracted in S202, the control part 313 extracts each biological sound generation interval that satisfies all of the following three conditions (S206).

The first condition is that the biological sound generation interval includes an amplitude of the hyoid bone displacement data whose proportion to the maximum amplitude thereof in the entire interval is greater than or equal to a predetermined proportion (for example, 3%). For example, in the example shown in FIG. 9C, an amplitude A1 of the hyoid bone displacement data in the biological sound generation interval is large. When the amplitude of the hyoid bone displacement data is large in the biological sound generation interval, the first condition is satisfied. During swallowing, the hyoid bone goes up, then, is displaced forward, and then, returns to its original position. The first condition is for determining, based on the hyoid bone displacement data, whether such a phenomenon has occurred in the biological sound generation interval.

The second condition is that, in the mel-frequency spectrogram of the biological sound generation interval, the proportion of the total sum (power) of the spectrum that is higher than or equal to 750 Hz is greater than or equal to a predetermined proportion (for example, 15%). Normally, swallowing sound contains high frequency (>750 Hz) components. The second condition is for determining, based on the biological sound data, whether the frequency of sound corresponding to swallowing sound has occurred in the biological sound generation interval. For example, with respect to the example shown in FIG. 10B, in the mel-frequency spectrogram of the biological sound generation interval, if the proportion of the total sum of the spectrum that is higher than or equal to 750 Hz exceeds 15%, the second condition is satisfied. It should be noted that the threshold is set to 750 Hz here, but this threshold can be changed to another frequency as appropriate, by taking statistics of actually measured values of swallowing sound.

The third condition is that the number of pulses generated in S205 in the biological sound generation interval is less than or equal to a predetermined number (for example, 50) and that the maximum width of the pulses generated in S205 in the biological sound generation interval is less than or equal to a predetermined value (for example, 15 msec). This is because swallowing sound can be distinguished from other sounds from the viewpoint of intermittency and continuity. The higher the intermittency is, the more pulses having short widths appear, and the higher the continuity is, the fewer pulses appear and the longer the pulse width becomes. The third condition is for determining, based on the biological sound data, whether intermittency and continuity of sound corresponding to swallowing sound have occurred in the biological sound generation interval. For example, with respect to the example shown in FIGS. 10C and 10D, in the biological sound generation interval, if the number of pulses N is less than or equal to 50, and the maximum pulse width W is less than or equal to 15 msec, the third condition is satisfied. It should be noted that the threshold for the number of pulses is set to 50, and the threshold for the maximum pulse width is set to 15 msec here, but the threshold for the number of pulses and the threshold for the maximum pulse width can be changed to another number and another time width as appropriate, by taking statistics of actually measured values of swallowing sound.

With reference to FIG. 7, next, the control part 313 sequentially refers to the biological sound generation intervals extracted in S206, and extracts intervals in which it can be estimated that swallowing sound has been generated, as described below.

First, the control part 313 sets, as a reference destination, the first biological sound generation interval among the biological sound generation intervals extracted in S206 (S207). Subsequently, the control part 313 sets a reference range sufficiently wider than this biological sound generation interval for the airflow pressure data, and determines whether a apneic interval longer than or equal to a predetermined period is included in this reference range (S208). In general, during swallowing, respiration stops. In S208, it is determined whether swallowing has occurred in the biological sound generation interval of the reference destination, from the viewpoint of respiration. In the determination in S208, the predetermined period is set to be longer than or equal to 400 msec, for example; and preferably, set to be longer than or equal to 500 msec, or longer than or equal to 600 msec. However, the predetermined period is not limited to these, and can be set to another value as long as the value can set the lower limit of the period in which respiration stops during swallowing.

Further, the control part 313 determines whether at least one of the pulses (pulses obtained in S205) that correspond to the biological sound generation interval of the reference destination is included in the apneic interval (S209). Here, it is determined whether sound has been detected in the apneic interval. That is, whether sound has been detected while respiration has stopped is used as a further swallowing estimation condition. When having determined as YES in both S208 and S209, the control part 313 estimates that the sound in the biological sound generation interval is swallowing sound, and specifies this biological sound generation interval as a swallowing sound generation interval (S210). On the other hand, when having determined as NO in either S208 or S209, the control part 313 determines that swallowing has not occurred in the biological sound generation interval (S211).

Subsequently, the control part 313 determines whether the processes of S208 to S211 have ended for all the biological sound generation intervals extracted in S206 (S212). When the processes of S208 to S211 have not ended (S212: NO), the control part 313 sets the next biological sound generation interval as the reference destination (S213) and returns the process to S208. In this manner, the processes of S208 to S211 are performed for all the biological sound generation intervals extracted in S206, whereby swallowing estimation is performed.

With reference to FIG. 8, next, the control part 313 sequentially refers to the swallowing sound generation intervals extracted in S210, and determines whether there is an aspiration risk in the swallowing sound generation interval concerned.

First, the control part 313 sets the first swallowing sound generation interval as a reference destination (S214). Subsequently, the control part 313 obtains respiratory phases immediately before and immediately after this swallowing sound generation interval (S215). Subsequently, the control part 313 determines whether the respiratory phase immediately before this swallowing sound generation interval is an inspiratory phase (S216), and further determines whether the respiratory phase immediately after this swallowing sound generation interval is an inspiratory phase (S217). When having determined as YES in either S216 or S217, the control part 313 determines that there is an aspiration risk in the swallowing sound generation interval (S218). On the other hand, when having determined as NO in both S216 and S217, the control part 313 determines that there is no aspiration risk in the swallowing sound generation interval (S219).

Subsequently, the control part 313 determines whether the processes of S215 to S219 have ended for all the swallowing sound generation intervals (S220). When the processes of S215 to S219 have not ended (S220: NO), the control part 313 sets the next swallowing sound generation interval as the reference destination (S221) and returns the process to S215. In this manner, with respect to all the swallowing sound generation intervals, whether there is an aspiration risk is determined.

Next, in response to an instruction from the operator inputted via the input part 330, the control part 313 performs a process of displaying, on the display part 320, a screen 410 (see FIG. 11), a screen 420 (see FIG. 12), and a screen 430 (see FIG. 13A) based on the above processes (S222). Then, the process performed by the information processing device 300 ends.

Figure 11:
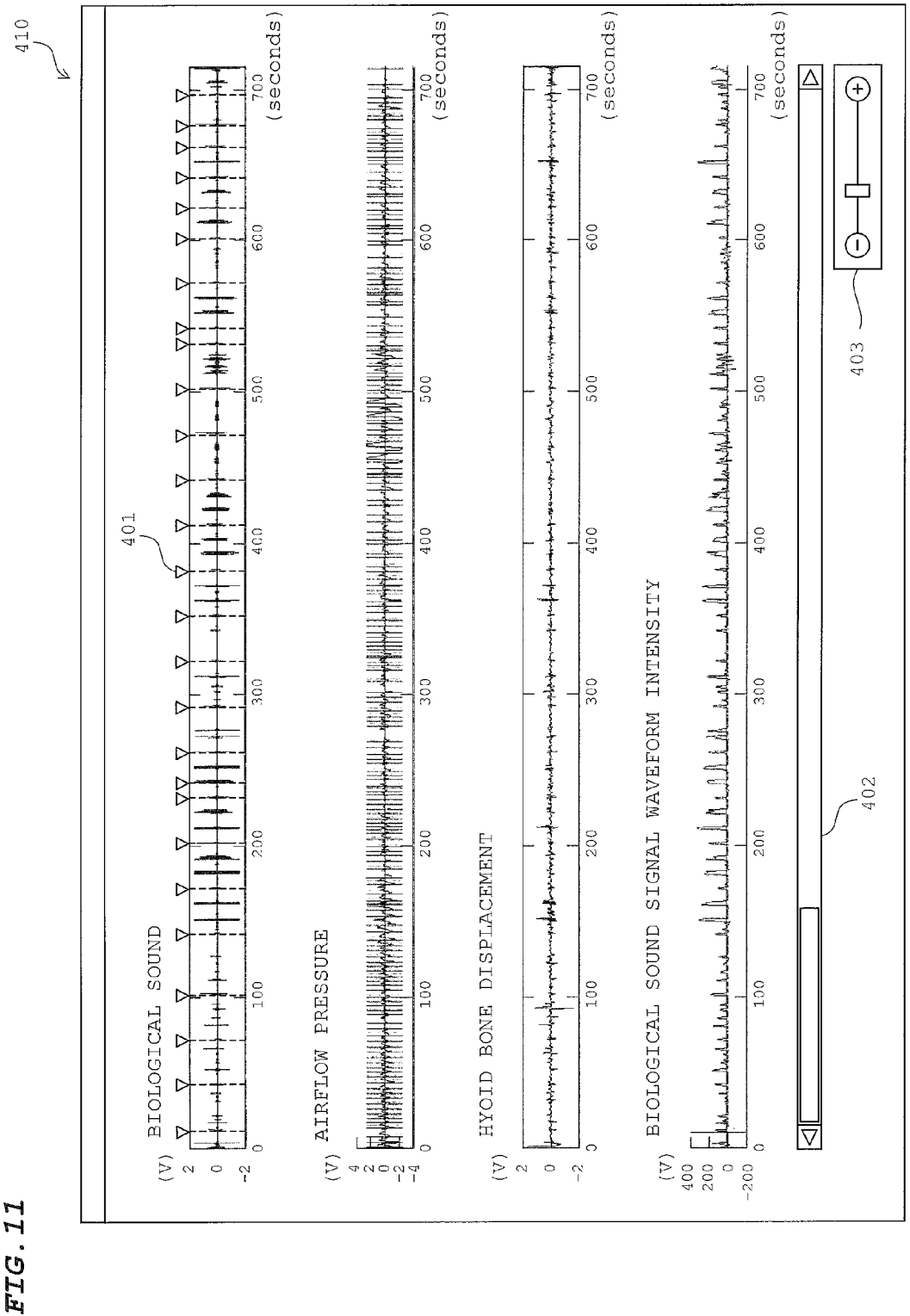
FIG. 11 shows a screen to be displayed on a display part according to Embodiment 2.

FIG. 11 shows the screen 410 displayed on the display part 320. The screen 410 includes icons 401, a reference position operation part 402, and a zoom-in/zoom-out operation part 403. In the screen 410, graphs of analog waveforms of the biological sound data, the airflow pressure data, and the hyoid bone displacement data, and a graph of biological sound signal waveform intensity are shown.

On the graph of the biological sound data, broken lines are shown at positions that correspond to the swallowing sound generation intervals, and the icons 401 are disposed above the broken lines, respectively. When an icon 401 is pressed, the screen 420 showing a zoomed-in state of the corresponding swallowing sound generation interval (see FIG. 12) is displayed on the display part 320. When the reference position operation part 402 is operated, the time ranges of the respective pieces of data displayed on the four graphs are moved in a direction of advancing or reversing the time in the entire measurement interval. When the zoom-in/zoom-out operation part 403 is operated, the time widths of the respective pieces of data displayed on the four graphs are extended/compressed.

Figure 12:
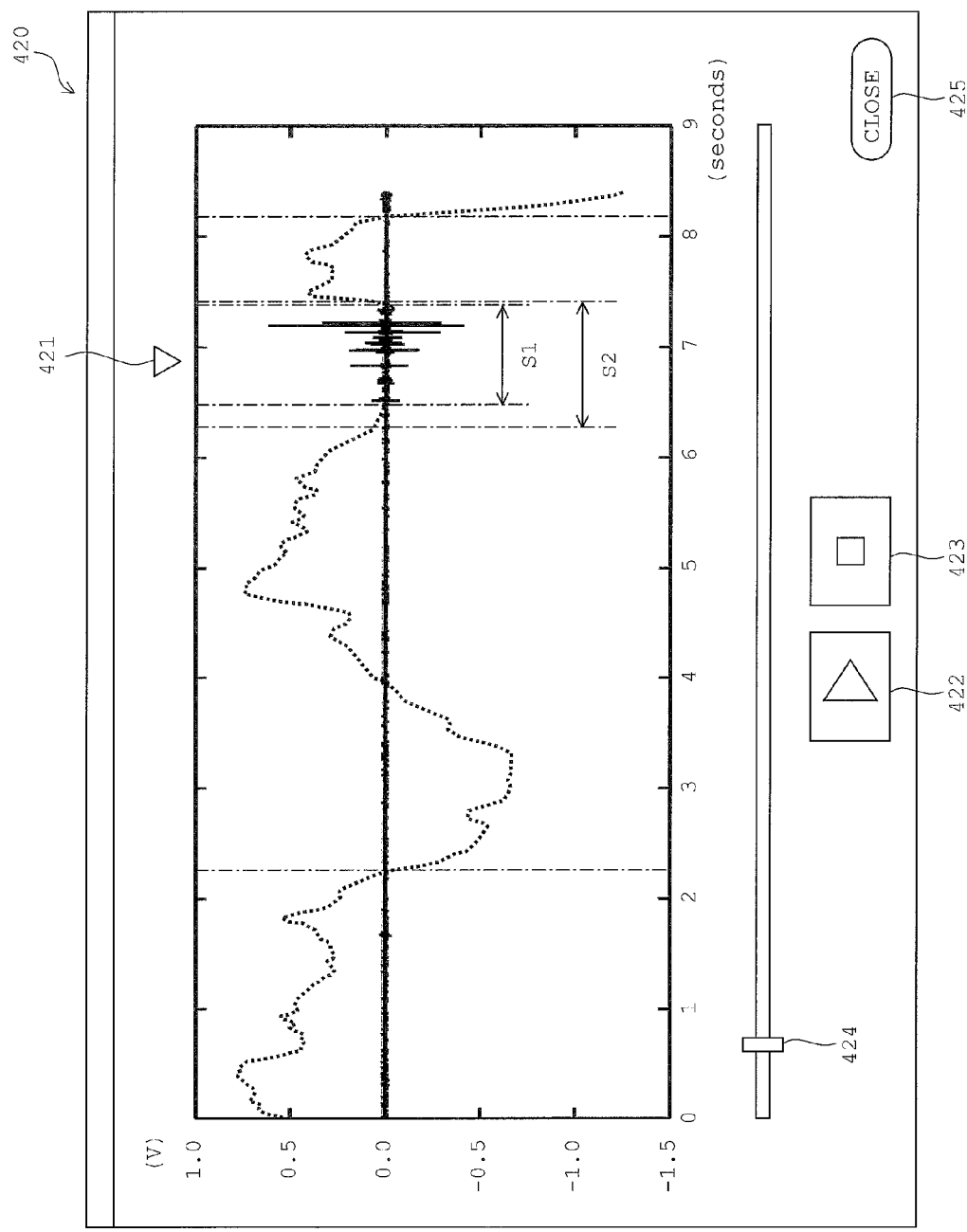
FIG. 12 shows a screen to be displayed on the display part according to Embodiment 2.

FIG. 12 shows the screen 420 to be displayed on the display part 320. The screen 420 includes an icon 421, a play button 422, a stop button 423, a reproduction position operation part 424, and a close button 425.

In the screen 420, the analog waveform of the biological sound data and the analog waveform of the airflow pressure data are shown in a superposed manner. Here, the analog waveform of the biological sound data is indicated with a solid line, and the analog waveform of the airflow pressure data is indicated with a dotted line. An interval S1 is a swallowing sound generation interval designated by the icon 401 in the screen 410 of FIG. 11, and the icon 421 indicates this interval. An interval S2 is an apneic interval in the vicinity of the interval S1.

When the play button 422 is pressed, sound that is obtained by reproducing the biological sound data of the interval S1 is outputted from the speaker 312. When the stop button 423 is pressed, the reproduction is stopped. The reproduction position operation part 424 indicates the position of the interval S1 of the sound to be reproduced in the entire measurement interval. When the reproduction position operation part 424 is operated, the position at which the reproduction is performed is changed in a direction of advancing or reversing the time.

FIG. 13A shows the screen 430 to be displayed on the display part 320.

The screen 430 shows: "the number of swallows" which indicates the number of swallowing sound generation intervals extracted in the entire measurement interval of the biological sound data; "the number of inspirations-swallows" which indicates the number of swallowing sound generation intervals that each have an inspiratory phase immediately therebefore; "the number of swallows-inspirations" which indicates the number of swallowing sound generation intervals that each have an inspiratory phase immediately thereafter; and "the number of aspiration risks" which indicates the number of swallowing sound generation intervals in which it has been determined that there had been an aspiration risk in S218 shown in FIG. 8.

As described above, according to Embodiment 2, whether swallowing has occurred is estimated based on the biological sound in an apneic state, and thus, the swallowing estimation accuracy can be increased. Accordingly, even if information for swallowing estimation is collected in a living environment, high swallowing estimation accuracy can be maintained. As a swallowing determination condition, values of parameters are used which indicate intermittency and continuity of sound, that is, the number and the lengths of pulses obtained by performing short-time Fourier transform and wavelet transform on the biological sound data. Thus, swallowing estimation can be performed with high accuracy through calculation. It should be noted that, among the biological sound generation intervals, only biological sound generation intervals that each correspond to an apneic interval are targeted for calculation. Accordingly, the calculation load is reduced, and swallowing estimation can be efficiently performed.

Moreover, biological sound generation intervals that each correspond to an apneic interval longer than or equal to 400 msec are targeted for swallowing estimation, whereby the swallowing estimation accuracy is further increased. Normally, during swallowing, respiration is stopped for a relatively long time. Thus, by causing the length of the non-respiration interval to be included in the estimation condition, the swallowing estimation accuracy is further increased.

As shown in S209, using as a further estimation condition whether at least one pulse is included in the apneic interval, it is estimated whether swallowing has occurred in the biological sound generation interval targeted for determination. Thus, since whether sound has been detected in a period where respiration has stopped is used as a further estimation condition, a high accuracy swallowing estimation result can be obtained.

Further, as shown in S206, in each biological sound generation interval, the proportion of sound having a frequency band higher than or equal to 750 Hz is calculated. By using as a further estimation condition whether the calculated proportion exceeds a predetermined proportion, it is estimated whether swallowing has occurred in the biological sound generation interval. Since the frequency components of sound are used as a further estimation condition, a high accuracy swallowing estimation result can be obtained.

As shown in S208, using as a further estimation condition whether the length of the apneic interval included in the biological sound generation interval exceeds a threshold, it is estimated whether swallowing has occurred in the biological sound generation interval. Since the length of the apneic interval included in the biological sound generation interval is used as a further estimation condition, a high accuracy swallowing estimation result can be obtained.

As shown in S206, using as a further estimation condition whether the biological sound generation interval includes an amplitude of the hyoid bone displacement data whose proportion to the maximum amplitude thereof in the entire interval is greater than or equal to a predetermined proportion, it is estimated whether swallowing has occurred in the biological sound generation interval. Since the amount of displacement of the larynx portion is used as a further estimation condition, a high accuracy swallowing estimation result can be obtained.

When the play button 422 is pressed in the screen 420, the biological sound data in the designated swallowing sound generation interval is reproduced. Thus, by actually listening to the sound at the timing at which it has been estimated that swallowing had occurred, a doctor or the like can confirm whether swallowing actually occurred at the timing. It should be noted that the reproduction interval of the biological sound data is not limited to the designated swallowing sound generation interval, and may be an interval having a time width previously set before and/or after the center of designated swallowing sound generation interval, for example. Alternatively, an interval obtained by adding a predetermined time width before and/or after the designated swallowing sound generation interval may be used as the reproduction interval of the biological sound data.

Further, in the screen 410, the icons 401 are disposed at positions that correspond to the swallowing sound generation intervals, respectively, and when an icon 401 is pressed, the screen 420 is displayed. Thus, the doctor or the like can easily designate the timing for which he or she would like to confirm, through sound, whether swallowing occurred.

In each of the screens 410 and 420, a graph of the analog waveform of the biological sound data is shown. Thus, the doctor or the like can appropriately designate the timing for which he or she would like to confirm, through sound, whether swallowing occurred, while confirming the sound waveform by viewing it.

When the icon 401 is pressed on the screen 410, a corresponding swallowing sound generation interval is displayed in the screen 420 in a zoomed-in manner. When the zoom-in/zoom-out operation part 403 is operated on the screen 410, the data displayed on the graph in the screen 410 can be zoomed-in. Thus, while confirming the sound waveform by viewing it, the doctor or the like can listen to the sound. This enables more appropriate determination of whether swallowing actually occurred at the timing.

As shown in FIG. 8, the respiratory phases before and after the timing at which it has been estimated that swallowing had occurred are detected; and based on the detected respiratory phases, it is evaluated whether there has been a possibility of aspiration at the timing. Then, the result of the evaluation is displayed in the screen 430. Thus, the doctor or the like can know whether it has been determined that there had been an aspiration risk for the subject by viewing the display, and thus, can utilize this knowledge in diagnosis for the subject.

Modification 1

In Embodiment 2, swallowing sound generation intervals are extracted by using three types of data, i.e., the biological sound data, the airflow pressure data, and the hyoid bone displacement data. However, in Modification 1, swallowing sound generation intervals are extracted by using the biological sound data and the airflow pressure data among the three types of data above.

In Modification 1, as shown in FIG. 13B, in the process performed by the information processing device 300 shown in FIG. 6, S206 is replaced with S301. In S301, different from Embodiment 2, the first condition using the hyoid bone displacement data is omitted.

FIG. 13C shows estimation results obtained when swallowing estimation was performed by actually collecting information for swallowing estimation.

Here, as shown in FIG. 4, the nasal cannula 220 and the pad 231 were attached to the subject, and information was collected in a living environment. The subject performs various actions spontaneously (in a pseudo manner) such as rotating the neck, coughing, uttering sounds, swallowing air, burping, sniffling, snoring, and deep breathing, in addition to swallowing. Then, every time performing such an action, the subject wrote down the time and the content of the action. In addition, in a room adjacent to the room of the subject, utterance and the like were made to generate household noises. Also with respect to such a noise, the time and the content were written down. Actions by the subject and generation of household noises were made 87 times in total. Among them, swallowing was conducted 27 times.

In FIG. 13C, swallowing estimation using "3 elements (Embodiment 2)" was performed in the following steps. In the following steps, the predetermined period was set to 600 msec.

(1) From the biological sound data, biological sound generation intervals are extracted by the method described above.

(2) In each biological sound generation interval, an apneic interval longer than or equal to the predetermined period is detected. Biological sound generation intervals in which an apneic interval longer than or equal to the predetermined period is not detected are not targeted for swallowing estimation.

(3) In each apneic interval longer than or equal to the predetermined period, the biological sound data is converted into pulses.

(4) With respect to each apneic interval longer than or equal to the predetermined period, the determination (using three parameters of hyoid bone displacement, biological sound frequency, and biological sound pulse) in S206 in FIG. 6 is conducted, and whether the biological sound generation interval is an estimated swallowing interval is determined.

It should be noted that the order of step (2) and step (3) may be switched with each other. In this case, conversion of the biological sound into pulses is performed on all the biological sound generation intervals. Then, an apneic interval longer than or equal to the predetermined period is detected for each biological sound generation interval. Then, whether the biological sound generation interval is an estimated swallowing interval is determined based on the widths and the number of the sound pulses in the apneic interval.

In FIG. 13C, with respect to "without hyoid bone (Modification 1)", in step (4) of the above algorithm, the parameter regarding displacement of the hyoid bone was omitted from the parameters used in the determination. With respect to "without sound (Comparative Example 1)", in step (4) of the above algorithm, the parameter based on the biological sound was omitted from the parameters used in the determination. Further, with respect to "without respiration (Comparative Example 2)", in the above algorithm, step (2) was omitted, the biological sound data was converted into pulses for all the biological sound generation intervals in step (3), and the determination in S206 in FIG. 6 was performed for all the biological sound generation intervals in step (4), whereby it was determined whether the biological sound generation interval concerned was an estimated swallowing interval.

The lines in FIG. 13C indicate, from the top: the number of swallows that were performed by the subject and that could be extracted through the estimation process; the number of swallows that were performed by the subject and that could not be extracted through the estimation process (non-extractions); the number of swallows that were not actually swallows but were determined as swallows through the estimation process (erroneous extractions); and the total thereof. The rows are, from left, estimation results obtained in Embodiment 2, Comparative Example 1, Comparative Example 2, and Modification 1.

With reference to FIG. 13C, in each of the estimation processes, all 27 swallows performed by the subject were correctly estimated as swallows. However, in Comparative Example where the airflow pressure (respiration) was not used as a parameter, actions other than swallowing and household noises were estimated as swallows as many as 36 times. This number greatly exceeds 27 which is the number of correct swallowing estimations. In contrast, in Embodiment 2, Comparative Example 1, and Modification 1 where the airflow pressure (respiration) was used as a parameter, occurrence of erroneous swallowing extraction was suppressed. In particular, in Embodiment 2 where three parameters including the airflow pressure (respiration) were used, the number of erroneous swallowing extractions was 7, which was a greatly reduced number.

The estimation results shown in FIG. 13C reveal that by causing the parameter of respiration to be included as a swallowing estimation condition, the rate of erroneous swallowing extraction is greatly reduced. In particular, as in Embodiment 2 above, by causing the parameter of biological sound and the parameter of hyoid bone displacement to be included in the swallowing estimation conditions as well as the parameter of respiration, occurrence of erroneous swallowing extraction can be remarkably suppressed and swallowing estimation can be performed with high accuracy.

With respect to the estimation results shown in FIG. 13C, in the estimation process in Embodiment 2, coughs by the subject were extracted as swallows. Since almost all the sound of a cough occurs during expiration, the sound of a cough is excluded in step (3), and theoretically, the cough is not determined as a swallow in normal situations. However, actually, coughs were estimated as swallows in the measurement. The reason for this is assumed as follows: in the measurement in FIG. 13C, each apneic interval was extracted in consideration of noise; thus, a small (greater than or equal to the predetermined period in steps (3) and (4)) expiration interval is included in the apneic interval; and due to the sound of a cough and the movement of the hyoid bone in this expiration interval, the cough was estimated as a swallow. Occurrence of such an erroneous extraction can be suppressed by further setting a condition "in the extracted biological sound interval, sound in the apneic interval is louder than sound in the respiration" in addition to the steps (1) to (4) above. This is because the sound of a cough at the start of expiration included in an apneic interval is louder in the expiration interval thereafter.

Modification 2

In Modification 2, among biological sound generation intervals, only biological sound generation intervals that each correspond to an apneic interval longer than or equal to a predetermined period are targeted for swallowing estimation.

Figure 14:
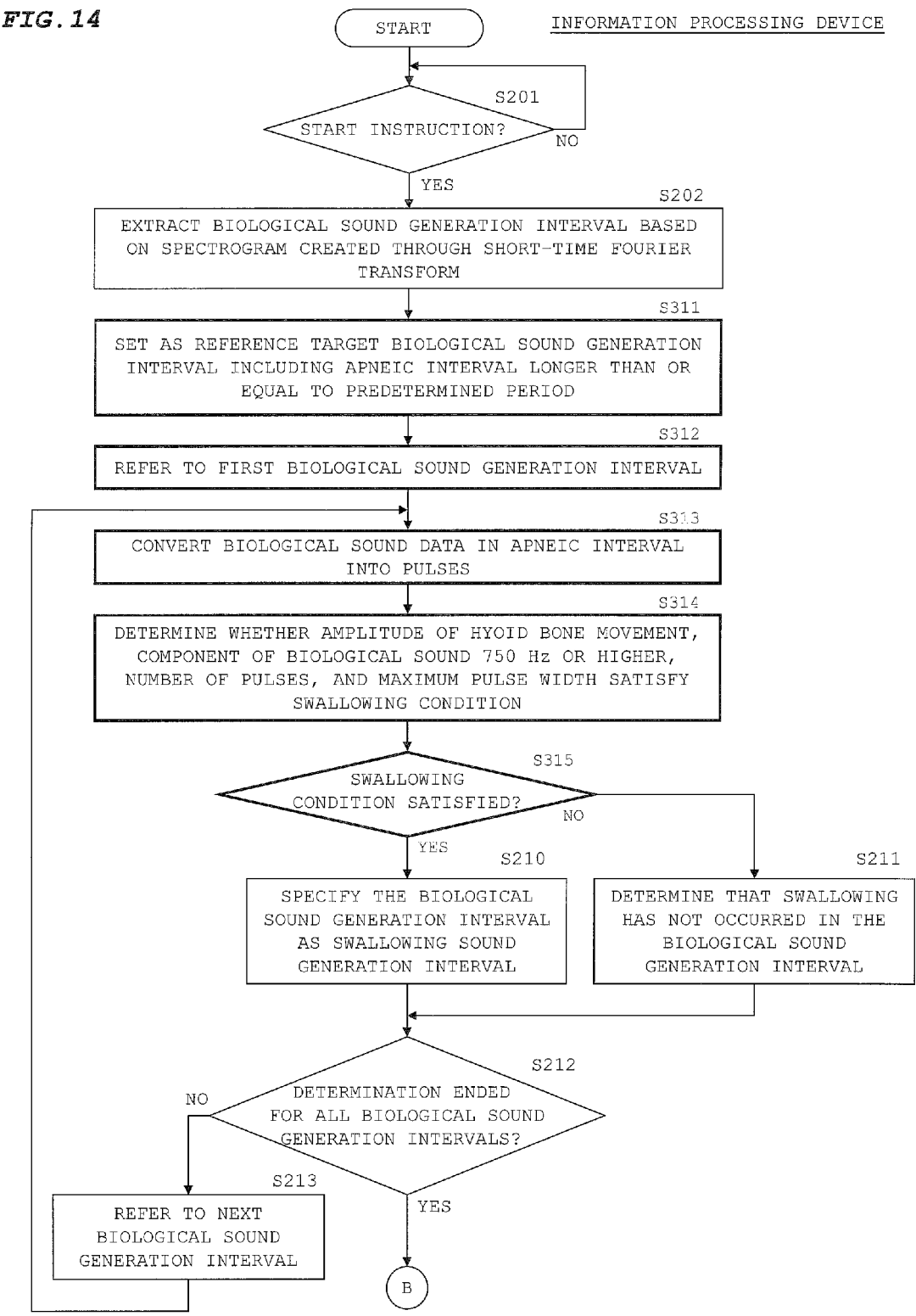
FIG. 14 is a flow chart showing operation performed by the information processing device according to Modification 2.

FIG. 14 is a flow chart showing the process performed in this case. In FIG. 14, S203 to S209 in the flow charts in FIGS. 6 and 7 are replaced with S311 to S315.

When biological sound generation intervals have been extracted from the biological sound data in S202, biological sound generation intervals, among the extracted biological sound generation intervals, that each include an apneic interval longer than or equal to a predetermined period are set as reference targets for swallowing estimation (S311). Among the biological sound generation intervals set as the reference targets, the first biological sound generation interval is referred to (S312), and the biological sound data included in the apneic interval in the biological sound generation interval is converted into pulses as in Embodiment 2 above (S313). Then, the swallowing condition in S206 in FIG. 6 is applied to the value of each parameter for this apneic interval (S314), and whether the values of all the parameters satisfy the swallowing condition is determined (S315). When the values of all the parameters satisfy the swallowing condition (S315: YES), it is determined that swallowing has occurred in the biological sound generation interval (S210). When the value of at least one parameter does not satisfy the swallowing condition (S315: NO), it is determined that swallowing has not occurred in the biological sound generation interval (S211).

In Modification 2, among biological sound generation intervals, only biological sound generation intervals that each include an apneic interval longer than or equal to a predetermined period are targeted for swallowing estimation. Accordingly, calculation load can be reduced, and swallowing estimation can be more efficiently performed.

Modification 3

In Modification 3, the control part 313 compares biological sound data in the respiratory phase immediately before each swallowing sound generation interval with biological sound data in the respiratory phase immediately after the swallowing sound generation interval, thereby determining whether aspiration has occurred in the swallowing sound generation interval.

Figure 15:
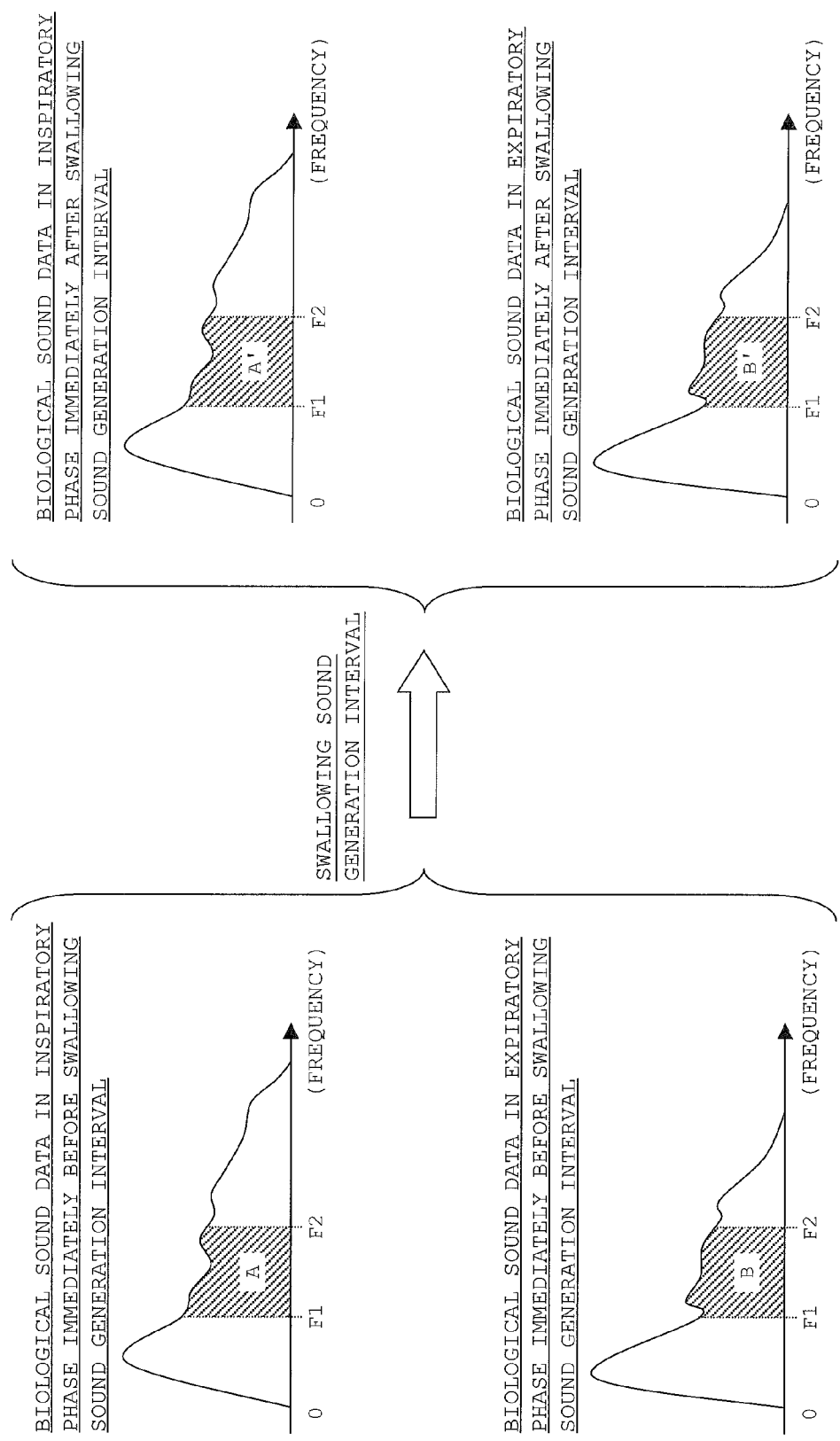
FIG. 15 is a diagram for explaining the procedure of determining whether aspiration has occurred according to Modification 3.

With reference to the left part of FIG. 15, the control part 313 performs Fourier transform on biological sound data in the inspiratory phase immediately before a swallowing sound generation interval and takes the integral from frequency F1 to frequency F2, thereby calculating a value A. Further, the control part 313 performs Fourier transform on biological sound data in the expiratory phase immediately before the swallowing sound generation interval and takes the integral from frequency F1 to frequency F2, thereby calculating a value B. Similarly, the control part 313 performs Fourier transform on biological sound data in the inspiratory phase immediately after the swallowing sound generation interval and takes the integral from frequency F1 to frequency F2, thereby calculating a value A'. Further, the control part 313 performs Fourier transform on biological sound data in the expiratory phase immediately after the swallowing sound generation interval and takes the integral from frequency F1 to frequency F2, thereby calculating a value B'.

Next, the control part 313 calculates a power ratio A/B based on the values obtained for the respiratory phases immediately before the swallowing sound generation interval, and a power ratio A'/B' based on the values obtained for the respiratory phases immediately after the swallowing sound generation interval. Then, when the power ratio A'/B' has increased by a predetermined amount (for example, 50%) from the power ratio A/B, the control part 313 determines that aspiration has occurred in the swallowing sound generation interval. In this manner, whether aspiration has occurred is determined with respect to all the swallowing sound generation intervals. Similarly to Embodiment 2, the number of aspiration risks in this case is also displayed in the screen 430 as shown in FIG. 13A.

According to Modification 3, inspiration sound and expiration sound before and after the timing at which it has been estimated that swallowing had occurred are detected. Then, based on the detected inspiration sound and expiration sound, it is evaluated whether there has been an aspiration risk at that timing. Then, the result of the evaluation is displayed in the screen 430. Thus, similarly to Embodiment 2, the doctor or the like can know whether it has been determined that there had been an aspiration risk for the subject by viewing the display, and thus, can utilize this knowledge in diagnosis for the subject.

Other Modifications

In S202 of Embodiment 2 and Modification 2, short-time Fourier transform is performed on biological sound data, then, the total sum of the amplitudes is calculated to obtain signal intensity, and then, the obtained signal intensity is compared with a threshold, whereby biological sound generation intervals are extracted. However, the method for extracting biological sound generation intervals is not limited thereto. For example, biological sound is subjected to full-wave rectification, then, to leak integration, and an interval that has a value exceeding the average+2SD (standard deviation) of the value in the soundless interval thereof may be defined as a biological sound generation interval. Also, the method for setting the threshold is not limited thereto, and as long as a biological sound generation interval can be extracted, another method may be used.

In Embodiment 2, various types of data is sent from the terminal device 210 to the information processing device 300 by means of the storage medium 101. However, the sending method is not limited thereto, and various types of data may be transmitted from the storage part of the terminal device 210 to the information processing device 300 over a wired or wireless communication network. Further, the terminal device 210 may have the function of the information processing device 300 and the information processing device 300 may be omitted. In this case, the control part 214 of the terminal device 210 performs all the processes performed by the information processing device shown in FIGS. 6 to 8, and outputs screens and the like showing results to the display part 211.

In addition to the above, various modifications can be made as appropriate, without departing from the scope of the technical idea defined by the claims.

From the embodiments above, an invention according to the claim below can also be derived. In this invention, parameters used in swallowing estimation are not limited to the parameters presented in the embodiments above. One or more of the parameters above can be combined together. Alternatively, other parameters can also be used. This claim can have claims 8 and 9 dependent therefrom.

<Claim>

A swallowing estimation device comprising:
a sound detection part configured to detect sound of a larynx portion;
a storage part in which sound information outputted from the sound detection part is stored;
a swallowing estimation part configured to estimate swallowing;
an output part configured to output information based on a result of the estimation performed by the swallowing estimation part; and
an input part capable of designating a timing at which the swallowing estimation part has estimated that swallowing had occurred, wherein
the output part obtains from the storage part the sound information having a time width including the timing designated via the input part, and outputs, to outside, sound that is obtained by reproducing the obtained sound information.

According to this invention, a significant effect can be obtained that the doctor or the like actually listens to the sound at the timing at which it has been estimated that swallowing had occurred, thereby being able to confirm whether swallowing actually occurred at the timing.

Moreover, from the embodiments above, an invention according to the claim below can also be derived. This claim can be dependent from claim 8 or 9.

<Claim>

A swallowing estimation device wherein
the output part obtains from the storage part the sound information having a time width including the timing designated via the input part, and displays a sound waveform based on the obtained sound information, in a zoomed-in manner.

According to this invention, the doctor or the like can listen to the sound, while confirming the sound waveform by viewing it. Accordingly, it is possible to more appropriately determine whether swallowing actually occurred at the timing.

INDUSTRIAL APPLICABILITY

The swallowing estimation device according to the present invention has an excellent swallowing estimation function, and can be used in the field of medical devices.

What is claimed is:

1. A swallowing estimation device comprising:
a sound detector that detects sound of a larynx portion;
a respiration detector that detects respiration;
a computer and a non-transitory storage medium containing a program for causing the computer to estimate swallowing based on sound information outputted from the sound detector and based on respiration information outputted from the respiration detector, wherein estimating swallowing comprises:
obtaining a value of a parameter for swallowing estimation with respect to a biological sound generation interval that corresponds to a respiratory cessation (apnea) interval longer than or equal to 400 msec; and
estimating whether swallowing has occurred in the biological sound generation interval based on whether the obtained value of the parameter satisfies a swallowing determination condition;
an output part configured to output information based on a result of the swallowing estimation performed, wherein the output part displays a screen in which a sound waveform based on the sound information outputted from the sound detector is superposed on a time axis, and a swallowing sound generation interval at which swallowing had been estimated to have occurred is indicated along the sound waveform;
a storage part in which the sound information outputted from the sound detector is stored; and
an input part capable of selecting, from the sound waveform displayed by the output part, the swallowing sound generation interval,
wherein the output part obtains from the storage part the sound information having a time width including the swallowing sound generation interval selected via the input part, and outputs sound that is obtained by reproducing the obtained sound information, and
when the swallowing sound generation interval is selected via the input part, the output part displays a zoomed-in state of the selected swallowing sound generation interval.

2. The swallowing estimation device according to claim 1, wherein the program further causes the computer to: detect, from the respiration information, respiratory phases before and after a timing at which swallowing had been estimated to have occurred, and evaluate whether there has been a possibility of aspiration at the timing based on the detected respiratory phases, and the output part outputs information based on a result of the evaluation.

3. The swallowing estimation device according to claim 1, wherein the program further causes the computer to: detect, from the sound information, inspiration sound and expiration sound before and after a timing at which swallowing had been estimated to have occurred, and evaluate whether there has been a possibility of aspiration at the timing based on the detected inspiration sound and expiration sound, and the output part outputs information based on a result of the evaluation.

4. The swallowing estimation device according to claim 1, wherein
when the swallowing sound generation interval is selected via the input part, the output part further displays an icon for selection by the input part to output the sound via the output part that reproduces biological sound data of the swallowing sound generation interval based on the sound information.

5. The swallowing estimation device according to claim 1, wherein
when the swallowing sound generation interval is selected via the input part, the output part displays a waveform of biological sound data based on the sound information superposed with a waveform of airflow pressure data based on the respiration information.

6. The swallowing estimation device according to claim 1, further comprising a displacement detector that detects displacement of the larynx portion, wherein
using as a further estimation condition whether an amount of the displacement of the larynx portion detected by the displacement detector in the biological sound generation interval exceeds a threshold, the program further causes the computer to estimate whether swallowing has occurred in the biological sound generation interval.

7. The swallowing estimation device according to claim 1, wherein
the sound detector includes at least one of a microphone and a sound sensor;
the respiration detector includes at least one of an air pressure sensor and a pressure sensor;
the storage part includes a hard disk;
the output part includes a display and a speaker; and
the input part includes at least one of a keyboard and a mouse.

8. A swallowing estimation device comprising:
a biological sound detector that detects biological sound at a larynx portion;
respiration detector that detects change in airflow of respiration;
a computer and a non-transitory storage medium containing a program for causing the computer to:
convert biological sound data obtained by sampling the biological sound into signal intensity data;
identify a signal interval having an intensity level higher than or equal to a noise level based on the signal intensity data;
identify an apneic interval based on airflow pressure data obtained by sampling change in the respiration;
obtain a signal intensity that corresponds to a sampling timing that is longer than or equal to a first predetermined period and that overlaps the signal interval, the sampling timing being in the apneic interval, and to generate a signal pulse having a width that corresponds to a period in which the signal intensity is greater than or equal to a predetermined level; and
estimate, as an estimated swallowing reflex interval, the apneic interval that satisfies a determination condition that the number of the signal pulses in the apneic interval longer than or equal to the first predetermined period is less than or equal to a predetermined number and a width of each signal pulse in the apneic interval longer than or equal to the first predetermined period is less than or equal to a second predetermined period;
an output part configured to display a screen in which a sound waveform based on the biological sound data is superposed on a time axis, and the estimated swallowing reflex interval at which swallowing had been estimated to have occurred is indicated along the sound waveform; and
an input part capable of selecting the estimated swallowing reflex interval indicated on the output part,
wherein the output part outputs sound that is obtained by reproducing the detected biological sound for the estimated swallowing reflex interval selected via the input part, and
when the estimated swallowing reflex interval is selected via the input part, the output part displays a zoomed-in state of the selected estimated swallowing reflex interval.

9. The swallowing estimation device according to claim 8, wherein
the biological sound detector includes at least one of a microphone and a sound sensor;
the respiration detector includes at least one of an air pressure sensor and a pressure sensor;
the output part includes a display and a speaker; and
the input part includes at least one of a keyboard and a mouse.

* * * * *